(12) United States Patent
Colletti et al.

(10) Patent No.: US 9,670,487 B2
(45) Date of Patent: Jun. 6, 2017

(54) CATIONIC LIPIDS FOR OLIGONUCLEOTIDE DELIVERY

(75) Inventors: Steven L. Colletti, Princeton Junction, NJ (US); Zhengwu James Deng, Eagleville, PA (US); Matthew G. Stanton, Marlton, NJ (US); Weimin Wang, Churchville, PA (US); Ivory Hills, Deerfield, MA (US)

(73) Assignee: SIRNA THERAPEUTICS, INC., Cambridge, MA (US)

( * ) Notice: Subject to any disclaimer, the term of this patent is extended or adjusted under 35 U.S.C. 154(b) by 85 days.

(21) Appl. No.: 13/574,315

(22) PCT Filed: Jan. 19, 2011

(86) PCT No.: PCT/US2011/021619
§ 371 (c)(1),
(2), (4) Date: Nov. 6, 2012

(87) PCT Pub. No.: WO2011/090965
PCT Pub. Date: Jul. 28, 2011

(65) Prior Publication Data
US 2013/0053572 A1 Feb. 28, 2013

Related U.S. Application Data

(60) Provisional application No. 61/298,022, filed on Jan. 25, 2010.

(51) Int. Cl.
| | |
|---|---|
| C07C 217/40 | (2006.01) |
| C12N 15/113 | (2010.01) |
| C07C 217/52 | (2006.01) |
| C07D 207/08 | (2006.01) |
| C07D 207/12 | (2006.01) |
| C07D 209/48 | (2006.01) |
| C07D 211/22 | (2006.01) |
| C07D 211/44 | (2006.01) |
| C07D 211/46 | (2006.01) |
| C07D 295/088 | (2006.01) |
| C07H 21/02 | (2006.01) |

(52) U.S. Cl.
CPC .......... *C12N 15/113* (2013.01); *C07C 217/40* (2013.01); *C07C 217/52* (2013.01); *C07D 207/08* (2013.01); *C07D 207/12* (2013.01); *C07D 209/48* (2013.01); *C07D 211/22* (2013.01); *C07D 211/44* (2013.01); *C07D 211/46* (2013.01); *C07D 295/088* (2013.01); *C07H 21/02* (2013.01); *C12N 15/1137* (2013.01); *C07C 2101/02* (2013.01); *C12N 2310/14* (2013.01); *C12N 2310/141* (2013.01); *C12N 2310/321* (2013.01); *C12N 2330/30* (2013.01)

(58) Field of Classification Search
CPC . C07C 217/40; C07C 217/52; C07C 2102/02; C07D 211/32; C07D 211/44; C07D 211/46; C07D 207/08; C07D 207/12; C07D 209/48; C07D 295/088; C07D 2102/02; C07H 21/02
USPC ....... 514/44 A; 424/450, 451; 564/292, 504; 546/242, 248; 548/543, 556, 570, 574
See application file for complete search history.

(56) References Cited

U.S. PATENT DOCUMENTS

| | | | |
|---|---|---|---|
| 4,124,641 A * | 11/1978 | Scherf ................ | B01D 17/047 544/177 |
| 8,569,256 B2 * | 10/2013 | Heyes et al. ................ | 514/44 A |
| 8,642,076 B2 * | 2/2014 | Manoharan et al. ......... | 424/451 |
| 2006/0008910 A1 | 1/2006 | MacLachlan et al. | |
| 2006/0083780 A1 | 4/2006 | Heyes et al. | |
| 2006/0240554 A1 | 10/2006 | Chen et al. | |
| 2008/0020058 A1 | 1/2008 | Chen et al. | |
| 2009/0023673 A1 | 1/2009 | Manoharan et al. | |
| 2009/0263407 A1 | 10/2009 | Dande et al. | |
| 2010/0015218 A1 | 1/2010 | Jadhav et al. | |
| 2011/0117125 A1 | 5/2011 | Hope et al. | |
| 2011/0250641 A1 * | 10/2011 | Powell et al. ............... | 435/69.1 |
| 2011/0256175 A1 | 10/2011 | Hope et al. | |
| 2012/0101148 A1 | 4/2012 | Aking et al. | |

FOREIGN PATENT DOCUMENTS

| | | | |
|---|---|---|---|
| WO | 2010048536 A2 | | 4/2010 |
| WO | WO2011090965 | * | 7/2011 |

OTHER PUBLICATIONS

Lee et al. "Novel molecular . . . " Biochem. J. vo. 387, 1-15 (2005).*
Wong et al. "Acid cleavable . . . " Mol. Biuosyst. p. 1-11 (2008).*
Zhang et al. "Interaction of . . . " CA155:163093 (2011).*
Brameld et al. "Small molecule . . . " J. Chem. Inf, Model. 48 p. 1-24 2008).*
Patani et al. "bioisosterism . . . " Chem. Rev. 96 p. 3147-3176 (1996).*
Rubini et al. "Synthesis of isosteric . . . " Tetrahedron 42(21) p. 6039-45 (1986).*
Anderson "Synthesis of amide bond . . . " p. 5 (2005).*
Chen et al. "From self assembled . . . " Col. Spring Harb Perspect Biol. vol. 2, p. a002170 (2010).*
Martin et al. "Design of cationic . . . " Current Pharm. design 11, 375-394 (2005).*
Pauly et al. "Latex and biological . . . " CA99:84760 (1983).*
Rubini et al. "Synthesis of isosteric . . . " Tetrhedron v.42921) 6039-6045 (1986).*
Mannard et al."Preparation of vesicles . . . " Methos in Enzymol. 372 p. 133-151 (2003).*

* cited by examiner

*Primary Examiner* — Celia Chang
(74) *Attorney, Agent, or Firm* — Nixon Peabody LLP

(57) ABSTRACT

The instant invention provides for novel cationic lipids that can be used in combination with other lipid components such as cholesterol and PEG-lipids to form lipid nanoparticles with oligonucleotides. It is an object of the instant invention to provide a cationic lipid scaffold that is susceptible to hydrolytic instability that may translate into reduced liver residence times and reduced hepatocellular toxicity. The present invention employs acetals and ketals to provide a low pH sensitive chemical handle for degradation.

7 Claims, 6 Drawing Sheets

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: 2' deoxy
<220> FEATURE:
<221> NAME/KEY: misc_feature
<222> LOCATION: (2)..(2)
<223> OTHER INFORMATION: 2' fluoro
<220> FEATURE:
<221> NAME/KEY: misc_feature
<222> LOCATION: (3)..(6)
<223> OTHER INFORMATION: 2' deoxy
<220> FEATURE:
<221> NAME/KEY: misc_feature
<222> LOCATION: (7)..(8)
<223> OTHER INFORMATION: 2' fluoro
<220> FEATURE:
<221> NAME/KEY: misc_feature
<222> LOCATION: (9)..(9)
<223> OTHER INFORMATION: 2' deoxy
<220> FEATURE:
<221> NAME/KEY: misc_feature
<222> LOCATION: (10)..(10)
<223> OTHER INFORMATION: 2' fluoro
<220> FEATURE:
<221> NAME/KEY: misc_feature
<222> LOCATION: (11)..(17)
<223> OTHER INFORMATION: 2' deoxy
<220> FEATURE:
<221> NAME/KEY: misc_feature
<222> LOCATION: (18)..(18)
<223> OTHER INFORMATION: 2' fluoro
<220> FEATURE:
<221> NAME/KEY: misc_feature
<222> LOCATION: (19)..(21)
<223> OTHER INFORMATION: 2' deoxy
<220> FEATURE:
<221> NAME/KEY: misc_feature
<222> LOCATION: (21)..(21)
<223> OTHER INFORMATION: inverted deoxy abasic

<400> SEQUENCE: 1
cuuuaacaau uccugaaaut t                                              21

<210> SEQ ID NO 2
<211> LENGTH: 21
<212> TYPE: RNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2' O-methyl
<220> FEATURE:
<221> NAME/KEY: misc_feature
<222> LOCATION: (4)..(9)
<223> OTHER INFORMATION: 2' fluoro
<220> FEATURE:
<221> NAME/KEY: misc_feature
<222> LOCATION: (10)..(10)
<223> OTHER INFORMATION: 2' O-methyl
<220> FEATURE:
<221> NAME/KEY: misc_feature
<222> LOCATION: (11)..(11)
<223> OTHER INFORMATION: 2' fluoro
<220> FEATURE:
<221> NAME/KEY: misc_feature
<222> LOCATION: (12)..(13)
<223> OTHER INFORMATION: 2' O-methyl
<220> FEATURE:
<221> NAME/KEY: misc_feature
<222> LOCATION: (14)..(17)
<223> OTHER INFORMATION: 2' fluoro
<220> FEATURE:
<221> NAME/KEY: misc_feature
<222> LOCATION: (18)..(18)
<223> OTHER INFORMATION: 2' O-methyl
<220> FEATURE:
<221> NAME/KEY: misc_feature
<222> LOCATION: (19)..(19)
<223> OTHER INFORMATION: 2' fluoro
<220> FEATURE:
<221> NAME/KEY: misc_feature
<222> LOCATION: (20)..(21)
<223> OTHER INFORMATION: 2' O-methyl

<400> SEQUENCE: 2
uaucucuuca uagccuuauu u                                          21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(4)
<223> OTHER INFORMATION: 2' O-methyl
<220> FEATURE:
<221> NAME/KEY: misc_feature
<222> LOCATION: (5)..(6)
<223> OTHER INFORMATION: 2' fluoro
<220> FEATURE:
<221> NAME/KEY: misc_feature
<222> LOCATION: (7)..(7)
<223> OTHER INFORMATION: 2' O-methyl
<220> FEATURE:
<221> NAME/KEY: misc_feature
<222> LOCATION: (8)..(9)
<223> OTHER INFORMATION: 2' fluoro
<220> FEATURE:
<221> NAME/KEY: misc_feature
<222> LOCATION: (10)..(14)
```

```
<223> OTHER INFORMATION: 2' O-methyl
<220> FEATURE:
<221> NAME/KEY: misc_feature
<222> LOCATION: (15)..(18)
<223> OTHER INFORMATION: 2' fluoro
<220> FEATURE:
<221> NAME/KEY: misc_feature
<222> LOCATION: (19)..(19)
<223> OTHER INFORMATION: 2' O-methyl
<220> FEATURE:
<221> NAME/KEY: misc_feature
<222> LOCATION: (20)..(21)
<223> OTHER INFORMATION: 2' deoxy
<220> FEATURE:
<221> NAME/KEY: misc_feature
<222> LOCATION: (20)..(21)
<223> OTHER INFORMATION: 2' deoxy
<220> FEATURE:
<221> NAME/KEY: misc_feature
<222> LOCATION: (20)..(21)
<223> OTHER INFORMATION: phosphorothioate linkagae
<220> FEATURE:
<221> NAME/KEY: misc_feature
<222> LOCATION: (21)..(21)
<223> OTHER INFORMATION: inverted deoxy abasic

<400> SEQUENCE: 3
cuuuaacaau uccugaaaut t                                          21

<210> SEQ ID NO 4
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: 2' O-methyl
<220> FEATURE:
<221> NAME/KEY: misc_feature
<222> LOCATION: (1)..(4)
<223> OTHER INFORMATION: phosphorothioate linkage
<220> FEATURE:
<221> NAME/KEY: misc_feature
<222> LOCATION: (6)..(10)
<223> OTHER INFORMATION: 2' fluoro
<220> FEATURE:
<221> NAME/KEY: misc_feature
<222> LOCATION: (11)..(12)
<223> OTHER INFORMATION: 2' O-methyl
<220> FEATURE:
<221> NAME/KEY: misc_feature
<222> LOCATION: (13)..(14)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
<222> LOCATION: (16)..(19)
<223> OTHER INFORMATION: 2' fluoro
<220> FEATURE:
<221> NAME/KEY: misc_feature
<222> LOCATION: (20)..(21)
<223> OTHER INFORMATION: 2' O-methyl
<220> FEATURE:
<221> NAME/KEY: misc_feature
<222> LOCATION: (20)..(21)
<223> OTHER INFORMATION: phosphorothioate linkage

<400> SEQUENCE: 4
auuucaggaa uuguuaaagu u                                          21
```

CATIONIC LIPIDS FOR OLIGONUCLEOTIDE DELIVERY

REFERENCE TO SEQUENCE LISTING SUBMITTED ELECTRONICALLY

The sequence listing of the present application is being submitted electronically via EFS-Web as an ASCII formatted sequence listing with a file name "MRLMIS00022USPCT -SEQTXT-19JUL. 2012.txt", creation date of Jul. 19, 2012 and a size of 4,265 bytes. This sequence listing submitted via EFS-Web is part of the specification and is herein incorporated by reference in its entirety.

BACKGROUND OF THE INVENTION

The present invention relates to novel cationic lipids that can be used in combination with other lipid components such as cholesterol and PEG-lipids to form lipid nanoparticles with oligonucleotides, to facilitate the cellular uptake and endosomal escape, and to knockdown target mRNA both in vitro and in vivo.

Cationic lipids and the use of cationic lipids in lipid nanoparticles for the delivery of oligonucleotides, in particular siRNA and miRNA, have been previously disclosed. (See US patent applications: US 2006/0008910, US 2006/0083780, US 2006/0240554, US 2008/0020058, US 2009/0263407 and US 2009/0285881 and PCT patent applications: WO 2009/086558, WO 2010/042877, WO 2010/048536, WO 2010/088537, and WO 2009/127060). See also Semple S. C. et al., Rational design of cationic lipids for siRNA delivery, Nature Biotechnology, published online 17 Jan. 2010; doi:10.1038/nbt.1602. Lipid nanoparticles and use of lipid nanoparticles for the delivery of oligonucleotides, in particular siRNA and miRNA, has been previously disclosed. (See US patent applications: US 2006/0240554 and US 2008/0020058). Oligonucleotides (including siRNA and miRNA) and the synthesis of oligonucleotides has been previously disclosed. (See US patent applications: US 2006/0240554 and US 2008/0020058).

Traditional cationic lipids such as DLinDMA have been employed for siRNA delivery to liver but suffer from extended tissue half lives. It is an object of the instant invention to provide a cationic lipid scaffold that is susceptible to hydrolytic instability that may translate into reduced liver residence times and reduced hepatocellular toxicity. The present invention employs acetals and ketals to provide a low pH sensitive chemical handle for degradation.

SUMMARY OF THE INVENTION

The instant invention provides for novel cationic lipids that can be used in combination with other lipid components such as cholesterol and PEG-lipids to form lipid nanoparticles with oligonucleotides. It is an object of the instant invention to provide a cationic lipid scaffold that is susceptible to hydrolytic instability that may translate into reduced liver residence times and reduced hepatocellular toxicity. The present invention employs acetals and ketals to provide a low pH sensitive chemical handle for degradation.

DETAILED DESCRIPTION OF THE INVENTION

Figure 1:
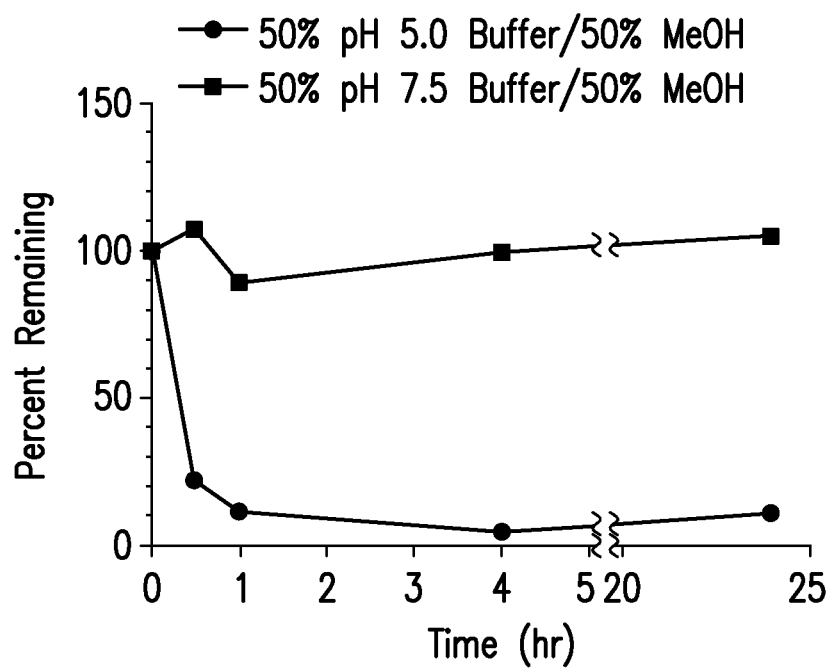
FIG. 1: Lipid (Compound 2) pH dependent hydrolytic stability.
Figure 2:
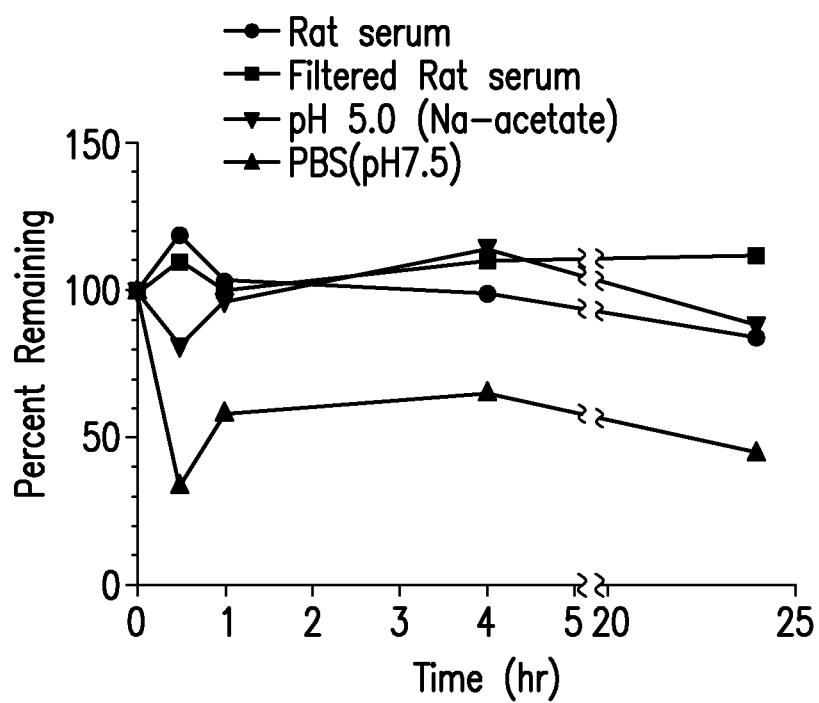
FIG. 2: Lipid (Compound 2) pH dependent hydrolytic stability within LNP assembly.

The various aspects and embodiments of the invention are directed to the utility of novel cationic lipids useful in lipid nanoparticles to deliver oligonucleotides, in particular, siRNA and miRNA, to any target gene. (See US patent applications: US 2006/0008910, US 2006/0083780, US 2006/0240554, US 2008/0020058, US 2009/0263407 and US 2009/0285881 and PCT patent applications: WO 2009/086558, WO 2010/042877, WO 2010/048536, WO 2010/088537, and WO 2009/127060). See also Semple S. C. et al., Rational design of cationic lipids for siRNA delivery, Nature Biotechnology, published online 17 Jan. 2010; doi:10.1038/nbt.1602.

The cationic lipids of the instant invention are useful components in a lipid nanoparticle for the delivery of oligonucleotides, specifically siRNA and miRNA.

In a first embodiment of this invention, the cationic lipids are illustrated by the Formula A:

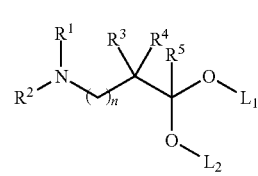

A wherein:

n is 0, 1 or 2;

$R^1$ and $R^2$ are independently selected from H, $(C_1-C_6)$ alkyl, heterocyclyl, and a polyamine, wherein said alkyl, heterocyclyl and polyamine are optionally substituted with one or more substituents selected from R', or $R^1$, and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one or more substituents selected from R';

$R^3$ is selected from H and $(C_1-C_6)$alkyl, wherein said alkyl is optionally substituted with one or more substituents selected from R', or $R^3$ can be taken together with $R^1$ to form a monocyclic heterocycle with 4-7 members optionally containing, in addition to the nitrogen, one or two additional heteroatoms selected from N, O and S, said monocyclic heterocycle is optionally substituted with one or more substituents selected from R';

$R^4$ is selected from H, $(C_1-C_6)$alkyl and O-alkyl, said alkyl is optionally substituted with one or more substituents selected from R';

$R^5$ is selected from H and $(C_1-C_6)$alkyl; or $R^5$ can be taken together with $R^1$ to form a monocyclic heterocycle with 4-7 members optionally containing, in addition to the nitrogen, one or two additional heteroatoms selected from N, O and S, said monocyclic heterocycle is optionally substituted with one or more substituents selected from R';

R' is independently selected from halogen, R", OR", SR", CN, $CO_2R"$ and $CON(R")_2$;

R" is selected from H and $(C_1-C_6)$alkyl, wherein said alkyl is optionally substituted with one or more substituents selected from halogen and OH;

$L_1$ is a $C_4-C_{22}$ alkenyl, said alkenyl is optionally substituted with one or more substituents selected from R'; and $L_2$ is a $C_4-C_{22}$ alkenyl, said alkenyl is optionally substituted with one or more substituents selected from R';

or any pharmaceutically acceptable salt or stereoisomer thereof.

In a second embodiment, the invention features a compound having Formula A, wherein:

$L_1$ and $L_2$ are

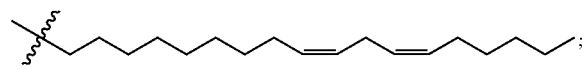 [SMILES: *CCCCCCCC/C=C\C/C=C\CCCCC]

and all other variables are as defined in the first embodiment;

or any pharmaceutically acceptable salt or stereoisomer thereof.

In another embodiment of this invention, the cationic lipids are illustrated by the Formula A:

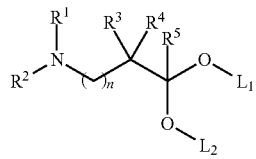

wherein:

n is 0, 1 or 2;

$R^1$ and $R^2$ are independently selected from H and $(C_1-C_4)$alkyl, wherein said alkyl is optionally substituted with one or more substituents selected from R', or $R^1$ and $R^2$ can be taken together with the nitrogen to which they are attached to form a monocyclic heterocycle which is optionally substituted with one or more substituents selected from R';

$R^3$ is selected from H and $(C_1-C_4)$alkyl, wherein said alkyl is optionally substituted with one or more substituents selected from R', or $R^3$ can be taken together with $R^1$ to form a monocyclic heterocycle which is optionally substituted with one or more substituents selected from R', or $R^3$ can be taken together with $R^4$ to form cyclopropyl or cyclobutyl;

$R^4$ is selected from H and $(C_1-C_4)$alkyl, said alkyl is optionally substituted with one or more substituents selected from R';

$R^5$ is selected from H and $(C_1-C_4)$alkyl, or $R^5$ can be taken together with $R^1$ to form a monocyclic heterocycle which is optionally substituted with one or more substituents selected from R';

R' is independently selected from halogen, R" and OR";

R" is selected from H and $(C_1-C_4)$alkyl, wherein said alkyl is optionally substituted with one or more substituents selected from halogen and OH;

$L_1$ is a $C_4-C_{22}$ alkyl or a $C_4-C_{22}$ alkenyl; and $L_2$ is a $C_4-C_{22}$ alkenyl;

or any pharmaceutically acceptable salt or stereoisomer thereof.

In another embodiment of this invention, the cationic lipids are illustrated by the Formula A:

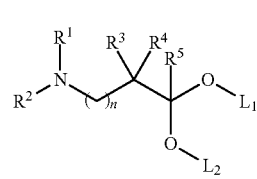

wherein:

n is 0, 1 or 2;

$R^1$ and $R^2$ are independently selected from H, methyl and ethyl, wherein said methyl and ethyl are optionally substituted with one or more substituents selected from R', or $R^1$ and $R^2$ can be taken together with the nitrogen to which they are attached to form a monocyclic heterocycle which is optionally substituted with one or more substituents selected from R';

$R^3$ is selected from H, methyl and ethyl, wherein said methyl and ethyl are optionally substituted with one or more substituents selected from R', or $R^3$ can be taken together with $R^1$ to form a monocyclic heterocycle which is optionally substituted with one or more substituents selected from R', or $R^3$ can be taken together with $R^4$ to form cyclopropyl;

$R^4$ is selected from H, methyl and ethyl, said methyl and ethyl are optionally substituted with one or more substituents selected from R';

$R^5$ is selected from H, methyl and ethyl, or $R^5$ can be taken together with $R^1$ to form a monocyclic heterocycle which is optionally substituted with one or more substituents selected from R';

R' is independently selected from OH and R";

R" is selected from H, methyl and ethyl, wherein said methyl and ethyl are optionally substituted with one or more substituents selected from halogen and OH;

$L_1$ is a $C_4-C_{22}$ alkyl or a $C_4-C_{22}$ alkenyl; and $L_2$ is a $C_4-C_{22}$ alkenyl;

or any pharmaceutically acceptable salt or stereoisomer thereof.

Specific cationic lipids are:

N,N-dimethyl-2,2-bis[(9Z,12Z)-octadeca-9,12-dien-1-yloxy]ethanamine (Compound 2);

N,N-dimethyl-2,2-bis[(9Z,12Z)-octadeca-9,12-dien-1-yloxy]propan-1-amine (Compound 3);

2,2-bis[(9Z,12Z)-octadeca-9,12-dien-1-yloxy]ethanamine (Compound 6);

(2R)-2-{bis[(9Z,12Z)-octadeca-9,12-dien-1-yloxy]methyl}pyrrolidine (Compound 8);

(2R)-2-{bis[(9Z,12Z)-octadeca-9,12-dien-1-yloxy]methyl}-1-methylpyrrolidine (Compound 9);

2-[(2R)-2-{bis[(9Z,12Z)-octadeca-9,12-dien-1-yloxy]methyl}pyrrolidin-1-yl]ethanol (Compound 10);

(2S)-1,1-bis[(9Z,12Z)-octadeca-9,12-dien-1-yloxy]propan-2-amine (Compound 11);

2-methyl-1,1-bis[(9Z,12Z)-octadeca-9,12-dien-1-yloxy]propan-2-amine (Compound 15);

4,4-bis[(9Z,12Z)-octadeca-9,12-dien-1-yloxy]piperidine (Compound 18);

3,3-bis[(9Z,12Z)-octadeca-9,12-dien-1-yloxy]pyrrolidine (Compound 19);
N,N-dimethyl-3,3-bis[(9Z,12Z)-octadeca-9,12-dien-1-yloxy]propan-1-amine (Compound 20):
1-{3,3-bis[(9Z,12Z)-octadeca-9,12-dien-1-yloxy]propyl}pyrrolidine (Compound 21);
3,3-bis[(9Z,12Z)-octadeca-9,12-dien-1-yloxy]propan-1-amine (Compound 22);
N,N-dimethyl-2,2-bis[(9Z)-octadec-9-en-1-yloxy]ethanamine (Compound 23);
1-{bis[(9Z,12Z)-octadeca-9,12-dien-1-yloxy]methyl}cyclopropanamine (Compound 28);
N,N-dimethyl-2-[(9Z,12Z)-octadeca-9,12-dien-1-yloxy]-2-(octyloxy)ethanamine (Compound 31);
2-(decyloxy)-N,N-dimethyl-2-[(9Z,12Z)-octadeca-9,12-dien-1-yloxy]ethanamine (Compound 32);
2-[(8Z)-dodec-8-en-1-yloxy]-N,N-dimethyl-2-[(9Z,12Z)-octadeca-9,12-dien-1-yloxy]ethanamine (Compound 33);
1-{2-[(8Z)-dodec-8-en-1-yloxy]-2-[(9Z,12Z)-octadeca-9,12-dien-1-yloxy]ethyl}pyrrolidine (Compound 34);
1-{2-[(9Z,12Z)-octadeca-9,12-dien-1-yloxy]-2-(octyloxy)ethyl}pyrrolidine (Compound 35);
[(2S)-1-{2-(decyloxy)-2-[(9Z,12Z)-octadeca-9,12-dien-1-yloxy]ethyl}pyrrolidin-2-yl]methanol (Compound 36);
1-{2-(decyloxy)-2-[(9Z,12Z)-octadeca-9,12-dien-1-yloxy]ethyl}piperidin-4-ol (Compound 37);
N,N-dimethyl-3-[(9Z,12Z)-octadeca-9,12-dien-1-yloxy]-3-(octyloxy)propan-1-amine (Compound 38);
2-(heptyloxy)-N,N-dimethyl-2-[(9Z,12Z)-octadeca-9,12-dien-1-yloxy]ethanamine (Compound 39);
N,N-dimethyl-2-(nonyloxy)-2-[(9Z,12Z)-octadeca-9,12-dien-1-yloxy]ethanamine (Compound 40);
1-{3-[(9Z,12Z)-octadeca-9,12-dien-1-yloxy]-3-(octyloxy)propyl}pyrrolidine (Compound 41);
2-(hexyloxy)-2-[(9Z,12Z)-octadeca-9,12-dien-1-yloxy]ethanamine (Compound 44);
2-[(9Z,12Z)-octadeca-9,12-dien-1-yloxy]-2-(octyloxy)ethanamine (Compound 45);
2-(decyloxy)-2-[(9Z,12Z)-octadeca-9,12-dien-1-yloxy]ethanamine (Compound 46);
2-(decyloxy)-2-[(9Z)-octadec-9-en-1-yloxy]ethanamine (Compound 47);
2-[(9Z,12Z)-octadeca-9,12-dien-1-yloxy]-2-(tetradecyloxy)ethanamine (Compound 48);
[(2R)-1-{2,2-bis[(9Z,12Z)-octadeca-9,12-dien-1-yloxy]ethyl}pyrrolidin-2-yl]methanol (Compound 49);
[(2S)-1-{2,2-bis[(9Z,12Z)-octadeca-9,12-dien-1-yloxy]ethyl}pyrrolidin-2-yl]methanol (Compound 50);
(3R,5S)-5-{bis[(9Z,12Z)-octadeca-9,12-dien-1-yloxy]methyl}pyrrolidin-3-ol (Compound 53);
(2S)-2-amino-3,3-bis[(9Z,12Z)-octadeca-9,12-dien-1-yloxy]propan-1-ol (Compound 54);
4-{bis[(9Z,12Z)-octadeca-9,12-dien-1-yloxy]methyl}piperidine (Compound 55);
3-{bis[(9Z,12Z)-octadeca-9,12-dien-1-yloxy]methyl}piperidine (Compound 56);
3-amino-1,1-bis[(9Z,12Z)-octadeca-9,12-dien-1-yloxy]propan-2-ol (Compound 61); and
1-methyl-4,4-bis[(9Z,12Z)-octadeca-9,12-dien-1-yloxy]piperidine (Compound 62)
or any pharmaceutically acceptable salt or stereoisomer thereof.

In another embodiment, the cationic lipids disclosed are useful in the preparation of lipid nanoparticles.

In another embodiment, the cationic lipids disclosed are useful components in a lipid nanoparticle for the delivery of oligonucleotides.

In another embodiment, the cationic lipids disclosed are useful components in a lipid nanoparticle for the delivery of siRNA and miRNA.

In another embodiment, the cationic lipids disclosed are useful components in a lipid nanoparticle for the delivery of siRNA.

The cationic lipids of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the cationic lipids disclosed herein may exist as tautomers and both tautomeric forms are intended to be encompassed by the scope of the invention, even though only one tautomeric structure is depicted.

It is understood that substituents and substitution patterns on the cationic lipids of the instant invention can be selected by one of ordinary skill in the art to provide cationic lipids that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

It is understood that one or more Si atoms can be incorporated into the cationic lipids of the instant invention by one of ordinary skill in the art to provide cationic lipids that are chemically stable and that can be readily synthesized by techniques known in the art from readily available starting materials.

In the compounds of Formula A, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula A. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula A can be prepared without undue experimentation by conventional techniques well known to those skilled in the art or by processes analogous to those described in the Scheme and Examples herein using appropriate isotopically-enriched reagents and/or intermediates.

As used herein, "alkyl" means a straight chain, cyclic or branched saturated aliphatic hydrocarbon having the specified number of carbon atoms.

As used herein, "alkenyl" means a straight chain, cyclic or branched unsaturated aliphatic hydrocarbon having the specified number of carbon atoms including but not limited to diene, triene and tetraene unsaturated aliphatic hydrocarbons.

Examples of a cyclic "alkyl" or "alkenyl" are:

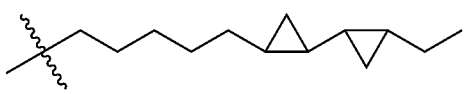

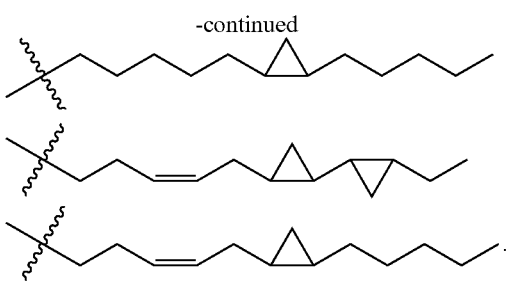

As used herein, "heterocyclyl" or "heterocycle" means an aromatic or nonaromatic heterocycle containing from 1 to 4 heteroatoms selected from the group consisting of O, N and S, and includes bicyclic groups. "Heterocyclyl" or "heterocycle" therefore includes, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof all of which are optionally substituted with one or more substituents selected from R'.

As used herein, "polyamine" means compounds having two or more amino groups. Examples include putrescine, cadaverine, spermidine, and spermine.

As used herein, "halogen" means Br, Cl, F and I.

In an embodiment of Formula A, n is 0.

In an embodiment of Formula A, n is 1.

In an embodiment of Formula A, n is 2.

In an embodiment of Formula A, $R^1$ and $R^2$ are independently selected from H and $(C_1-C_6)$alkyl, wherein said alkyl is optionally substituted with one or more substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one or more substituents selected from R'.

In an embodiment of Formula A, $R^1$ and $R^2$ are independently selected from H, methyl, ethyl and propyl, wherein said methyl, ethyl and propyl are optionally substituted with one or more substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one or more substituents selected from R'.

In an embodiment of Formula A, $R^1$ and $R^2$ are independently selected from H, methyl, ethyl and propyl.

In an embodiment of Formula A, $R^1$ and $R^2$ are independently selected from H and methyl.

In an embodiment of Formula A, $R^1$ and $R^2$ are both methyl.

$R^3$ is selected from H, methyl, ethyl and propyl, wherein said methyl, ethyl and propyl are optionally substituted with one or more substituents selected from R', or $R^3$ can be taken together with $R^1$ to form a monocyclic heterocycle with 4-7 members optionally containing, in addition to the nitrogen, one or two additional heteroatoms selected from N, O and S, said monocyclic heterocycle is optionally substituted with one or more substituents selected from R'.

$R^3$ is selected from H, methyl, ethyl and propyl, wherein said methyl, ethyl and propyl are optionally substituted with one or more substituents selected from R', or $R^3$ can be taken together with $R^1$ to form a monocyclic heterocycle which is optionally substituted with one or more substituents selected from R', or $R^3$ can be taken together with $R^4$ to form cyclopropyl or cyclobutyl.

In an embodiment of Formula A, $R^3$ is selected from H, methyl, ethyl and propyl.

In an embodiment of Formula A, $R^3$ is selected from H, methyl and ethyl.

In an embodiment of Formula A, $R^3$ is methyl.

In an embodiment of Formula A, $R^3$ is H.

In an embodiment of Formula A, $R^4$ is selected from H, methyl, ethyl and propyl.

In an embodiment of Formula A, $R^4$ is selected from H and methyl.

In an embodiment of Formula A, $R^4$ is methyl.

In an embodiment of Formula A, $R^4$ is H.

In an embodiment of Formula A, $R^5$ is selected from H, methyl, ethyl and propyl, wherein said methyl, ethyl and propyl are optionally substituted with one or more substituents selected from R', or $R^5$ can be taken together with $R^1$ to form a monocyclic heterocycle with 4-7 members optionally containing, in addition to the nitrogen, one or two additional heteroatoms selected from N, O and S, said monocyclic heterocycle is optionally substituted with one or more substituents selected from R'.

In an embodiment of Formula A, $R^5$ is selected from H, methyl, ethyl and propyl, wherein said methyl, ethyl and propyl are optionally substituted with one or more substituents selected from R', or $R^5$ can be taken together with $R^1$ to form a monocyclic heterocycle which is optionally substituted with one or more substituents selected from R'.

In an embodiment of Formula A, $R^5$ is selected from H, methyl, ethyl and propyl.

In an embodiment of Formula A, $R^5$ is selected from H and methyl.

In an embodiment of Formula A, $R^5$ is methyl.

In an embodiment of Formula A, $R^5$ is H.

In an embodiment of Formula A, R' is OH and R".

In an embodiment of Formula A, R' is R".

In an embodiment of Formula A, R" is selected from H, methyl, ethyl and propyl, wherein said methyl, ethyl and propyl are optionally substituted with one or more OH.

In an embodiment of Formula A, R" is selected from H, methyl and ethyl wherein said methyl and ethyl are optionally substituted with one or more OH.

In an embodiment of Formula A, $L_1$ is selected from $C_4-C_{22}$ alkyl and $C_4-C_{22}$ alkenyl, which are optionally substituted with halogen and OH.

In an embodiment of Formula A, $L_1$ is selected from $C_4-C_{22}$ alkyl and $C_4-C_{22}$ alkenyl.

In an embodiment of Formula A, $L_1$ is selected from $C_6$-$C_{18}$ alkyl and $C_6$-$C_{18}$ alkenyl.

In an embodiment of Formula A, $L_2$ is a $C_4$-$C_{24}$ alkenyl, which is optionally substituted with halogen and OH.

In an embodiment of Formula A, $L_2$ is a $C_4$-$C_{24}$ alkenyl.

In an embodiment of Formula A, $L_2$ is $C_{18}$ alkenyl.

In an embodiment of Formula A, $L_2$ is

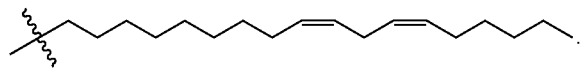

In an embodiment of Formula A, $L_1$ and $L_2$ are

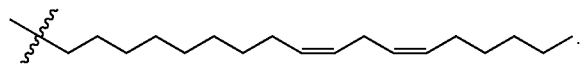 [SMILES: *CCCCCCCC/C=C\C/C=C\CCCCC]

In an embodiment of Formula A, "heterocyclyl" is pyrrolidine, piperidine, morpholine, imidazole or piperazine.

In an embodiment of Formula A, "monocyclic heterocycle" is pyrrolidine, piperidine, morpholine, imidazole or piperazine.

In an embodiment of Formula A, "monocyclic heterocycle" is pyrrolidine or piperidine.

In an embodiment of Formula A, "polyamine" is putrescine, cadaverine, spermidine or spermine.

In an embodiment, "alkyl" is a straight chain saturated aliphatic hydrocarbon having the specified number of carbon atoms.

In an embodiment, "alkenyl" is a straight chain unsaturated aliphatic hydrocarbon having the specified number of carbon atoms.

Included in the instant invention is the free form of cationic lipids of Formula A, as well as the pharmaceutically acceptable salts and stereoisomers thereof. Some of the isolated specific cationic lipids exemplified herein are the protonated salts of amine cationic lipids. The term "free form" refers to the amine cationic lipids in non-salt form. The encompassed pharmaceutically acceptable salts not only include the isolated salts exemplified for the specific cationic lipids described herein, but also all the typical pharmaceutically acceptable salts of the free form of cationic lipids of Formula A. The free form of the specific salt cationic lipids described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant cationic lipids can be synthesized from the cationic lipids of this invention which contain a basic or acidic moiety by conventional chemical methods. Generally, the salts of the basic cationic lipids are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the cationic lipids of this invention include the conventional non-toxic salts of the cationic lipids of this invention as formed by reacting a basic instant cationic lipids with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the cationic lipids of the present invention are acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the cationic lipids of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

EXAMPLES

Examples provided are intended to assist in a further understanding of the invention. Particular materials employed, species and conditions are intended to be further illustrative of the invention and not limitative of the reasonable scope thereof. The reagents utilized in synthesizing the cationic lipids are either commercially available or are readily prepared by one of ordinary skill in the art.

Synthesis of the novel cationic lipids is a linear process starting with acetal/ketal formation followed by amine displacement of the alkyl bromide.

GENERAL SCHEME 1

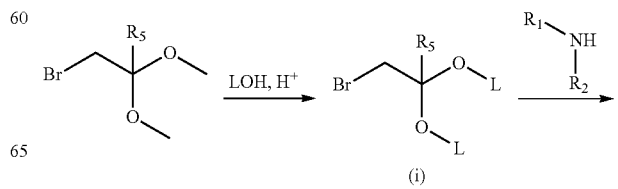

(i)

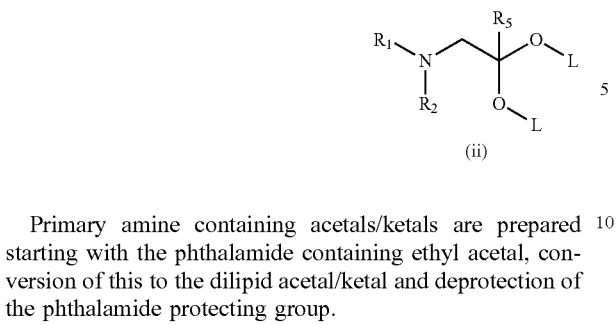

Primary amine containing acetals/ketals are prepared starting with the phthalamide containing ethyl acetal, conversion of this to the dilipid acetal/ketal and deprotection of the phthalamide protecting group.

GENERAL SCHEME 2

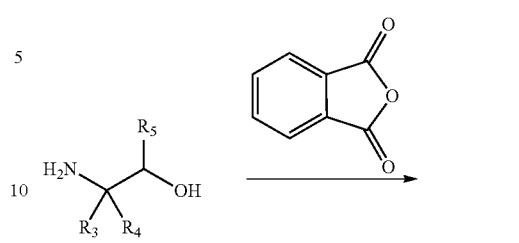

GENERAL SCHEME 4

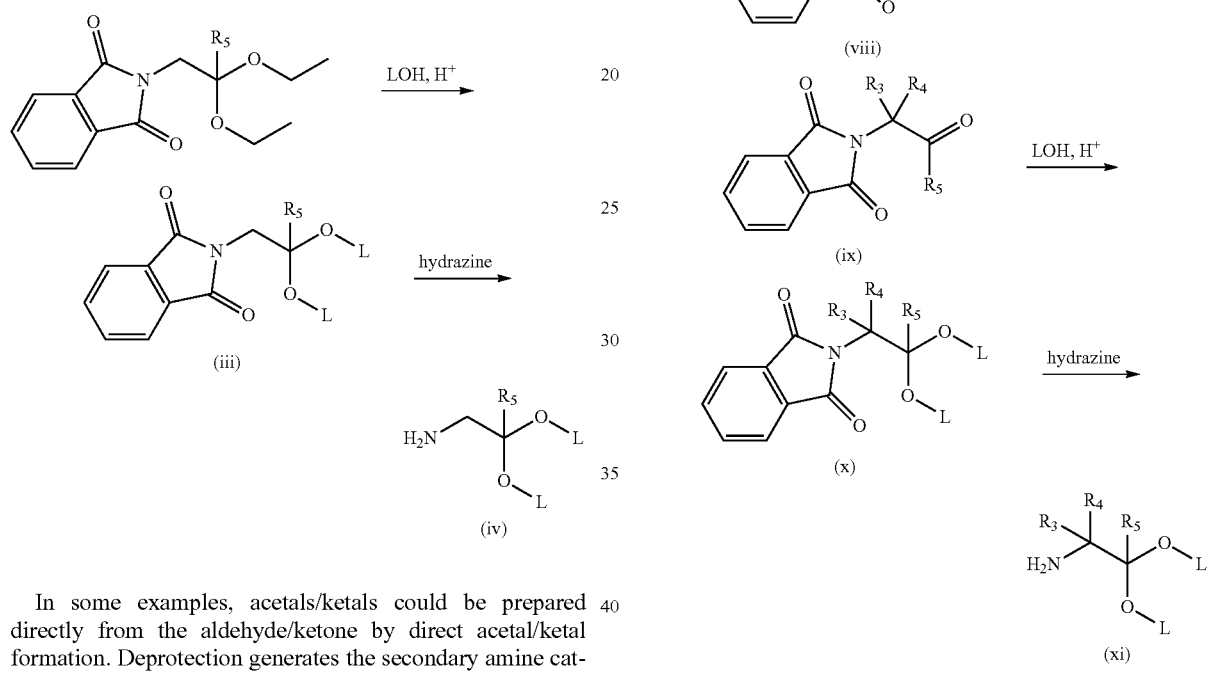

In some examples, acetals/ketals could be prepared directly from the aldehyde/ketone by direct acetal/ketal formation. Deprotection generates the secondary amine cationic lipids. Reductive amination gives tertiary amine cationic lipids.

GENERAL SCHEME 3

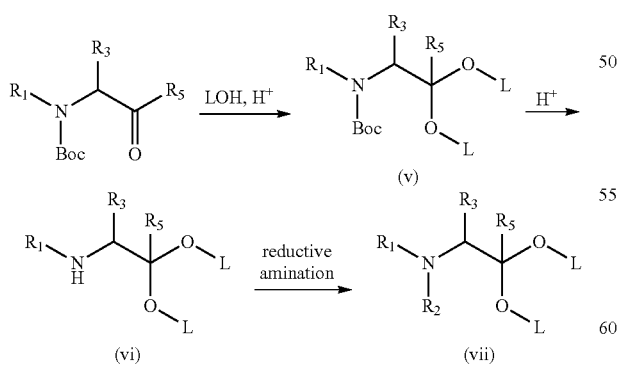

Geminally di-substituted cationic lipids are prepared by protecting the starting aminoalcohol as the phthalamide and then oxidizing the alcohol to the ketone. Acetal/ketal formation was followed by deprotection with hydrazine.

Cyclic ketals were prepared by first protecting the free amine of the diethyl ketal followed by ketalization with the lipid alcohol. Deprotection of the amine gives the free secondary amine. Reductive amination provides the tertiary amine cationic lipids.

GENERAL SCHEME 5

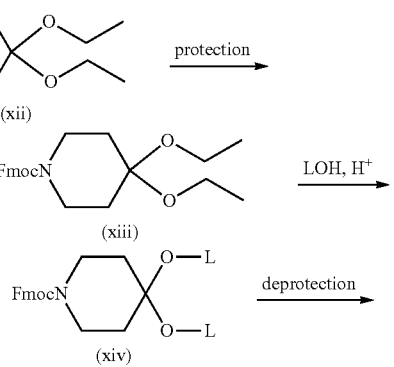

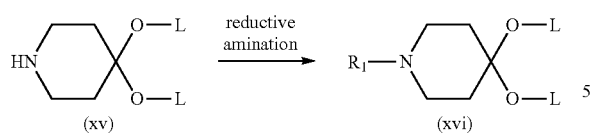

General scheme 6 is an extension of General Scheme 1 wherein the alkyl bromide is homologated.

GENERAL SCHEME 6

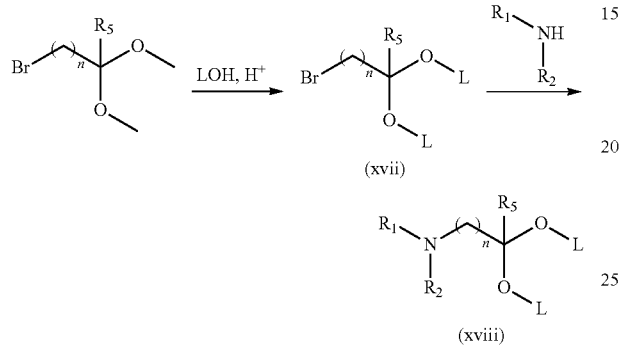

General Scheme 7 is an extension of General Scheme 6 wherein the alkylating agent is a phthalamide protected primary amine. Deprotection of this amine with hydrazine reveals cationic lipids of type xx.

GENERAL SCHEME 7

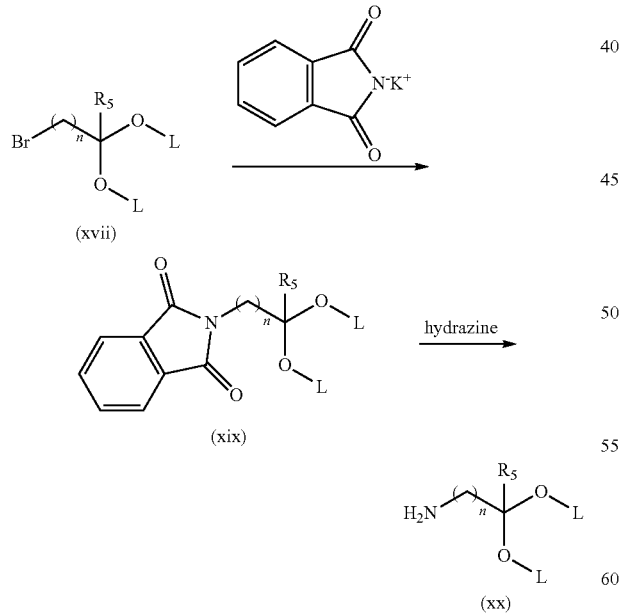

General scheme 8 is an extension of General Scheme 4 wherein the intermediate aldehyde/ketone ix is accessed via the Weinreb amide xxi. The Weinreb amide is prepared from ester xxi.

GENERAL SCHEME 8

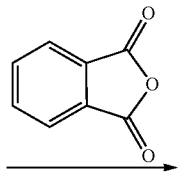

General scheme 9 outlines the preparation of mixed acetals of type xxv. The dimethyl acetal is first converted to a mixed lipid/methyl acetal using TMSOTf/lutidine followed by addition of lipid alcohol. The final mixed acetal is prepared by converting the intermediate mixed acetal xxiii to mixed lipid acetal xxiv employing similar conditions. Finally, the bromide is displaced with an amine to provide the final lipids.

GENERAL SCHEME 9

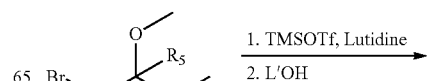

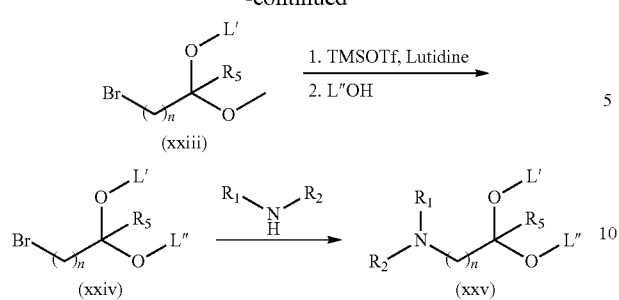

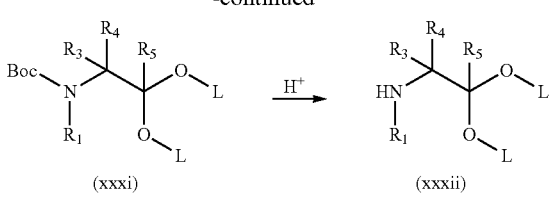

General Scheme 12 outlines the preparation of amino alcohol cationic lipids of type xxvi. Commercial epoxide xxxiii is opened with azide to give azido alcohol xxxiv. Lipid acetal formation followed by reduction of the azide delivers final compounds.

General Scheme 10 is analogous to General Scheme 9 wherein the starting material is a phthalamide protected amine acetal. Iterative mixed acetal formation followed by deprotection of the amine generates final compounds of type xxviii.

GENERAL SCHEME 10

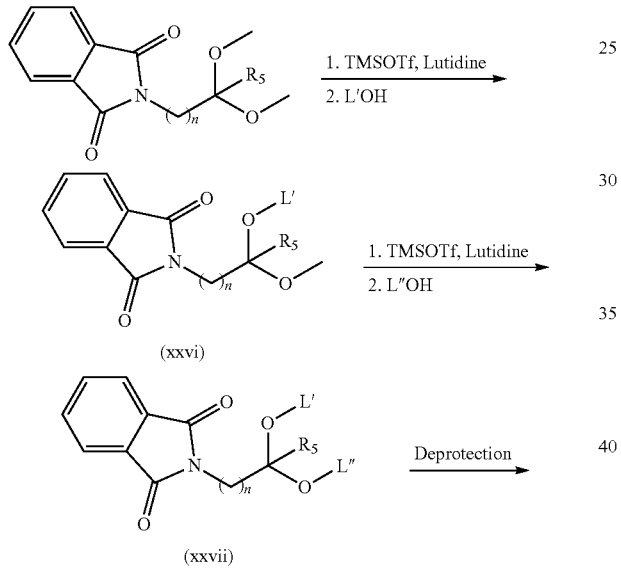

GENERAL SCHEME 12

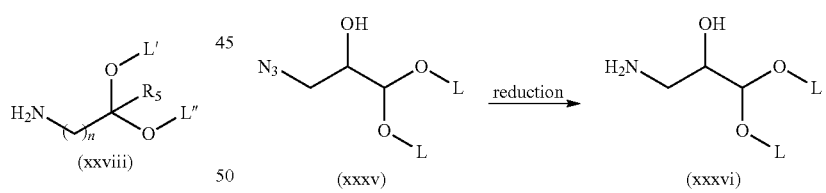

General Scheme 11 outlines preparation of lipids of type xxxii from commercially available alcohols xxix. Oxidation of the alcohol affords aldehyde or ketones of type xxx. Acetal/ketal formation followed by Boc deprotection provides the final compounds.

General Scheme 13 outlines the preparation of ketals of type xxxviii from the corresponding ketones xxxvii using acid and lipid alcohol.

GENERAL SCHEME 11

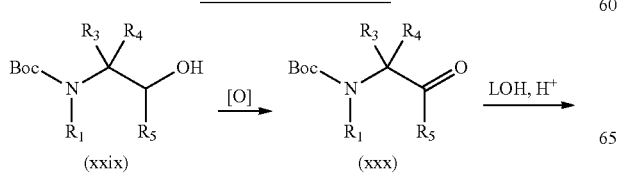

GENERAL SCHEME 13

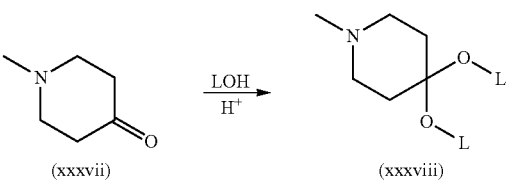

Schemes (6Z,9Z)-18-{2-bromo-1-[(9Z,12Z)-octadeca-9,12-dien-1-yloxy]ethoxy}octadeca-6,9-diene (Compound 1)

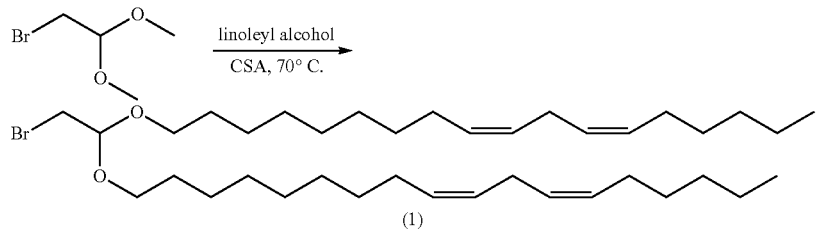

To a stirred mixture of bromoacetaldehyde dimethylacetal (1.0 g, 5.92 mmol) and linoleyl alcohol (3.15 g, 11.83 mmol) was added camphor sulfonic acid (0.07 g, 0.296 mmol) in one portion. The mixture heated to 70° C. for several hours. The reaction mixture was loaded directly onto a silica column and purified by flash chromatography to give product (2.5 g) in 66% yield. $^1$H NMR (400 MHz, CDCl$_3$) δ 5.34 (4H, m), 4.63 (1H, t, J=5.5), 3.60 (2H, m), 3.47 (2H, m), 3.35 (2H, J=5.5), 2.76 (4H, t, J=6.5), 2.03 (8H, q, J=6.3), 1.58 (4H, br m), 1.4-1.22 (32H, br m), 0.88 (6H, t, J=6.6) ppm.

N,N-dimethyl-2,2-bis[(9Z,12Z)-octadeca-9,12-dien-1-yloxy]ethanamine (Compound 2)

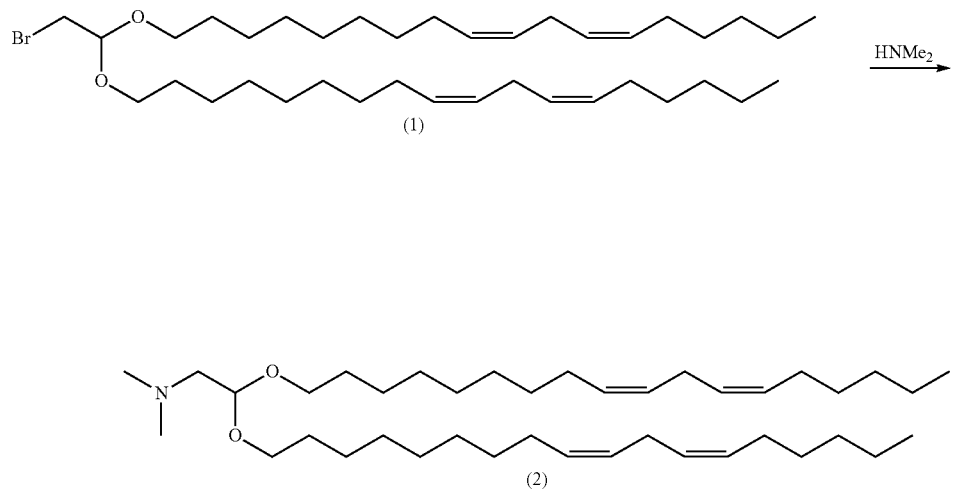

A solution of the bromide (1, 3.5 g, 5.49 mmol) in 0.89 g/mL dimethylamine in DMF (0.278 mL, 5.49 mmol) was heated to 150° C. under microwave irradiation for 30 minutes. The reaction was partitioned between water/ethyl acetate. The organics were washed with brine, dried over sodium sulfate, filtered and evaporated in vacuo to generate pure product (2, 2.6 g) in 79% yield. 1H NMR (400 MHz, CDCl3) δ 5.33 (8H, m), 4.56 (1H, t, J=5.5), 3.57 (2H q, J=7.5), 3.47 (2H q, J=7.5), 2.44 (2H d, J=5.4), 2.27 (6H, s), 1.56 (4H br m), 1.4-1.22 (32H, br m), 0.88 (6H, t, J=6.6) ppm.

N,N-dimethyl-2,2-bis[(9Z,12Z)-octadeca-9,12-dien-1-yloxy]propan-1-amine (Compound 3)

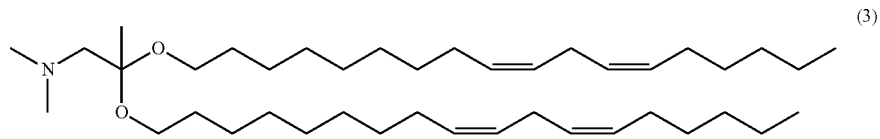 [SMILES: CCCCC/C=C\C/C=C\CCCCCCCCOC(C)(CN(C)C)OCCCCCCCC/C=C\C/C=C\CCCCC]

(3)

Compound 3 can be prepared according to General Scheme 1 above.

1.0 g, 33% yield. C41H77NO2: HRMS (ESI positive) M+H, theory m/z 616.6027, measured m/z 616.6038 amu. $^1$H NMR (400 MHz, CDCl$_3$) δ 5.35, (m, 8H), 3.40 (t, 4H, J=6.83 Hz), 2.77 (t, 4H, J=6.59 Hz), 2.42 (s, 3H), 2.29 (s, 6H), 2.05 (q, 8H, J=6.84 Hz), 1.51 (m, 2H), 1.30 (m, 36H), 0.89 (t, 6H, J=6.83 Hz) ppm.

Compound 4 is S-Octyl CLinDMA which is generically described in U.S. Pat. No. 7,514,099.

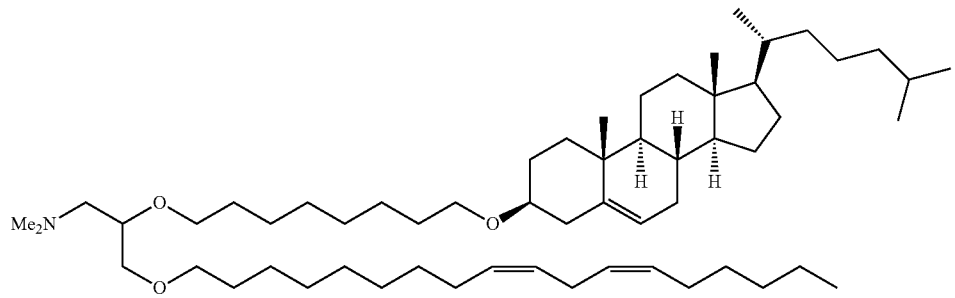

Compound 4

2-{2,2-bis[(9Z,12Z)-octadeca-9,12-dien-1-yloxy]ethyl}-1H-isoindole-1,3(2H)-dione (Compound 5)

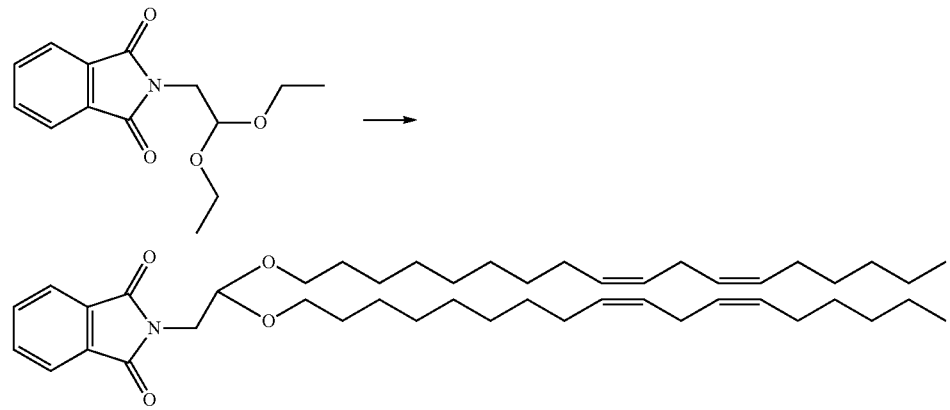

(5)

To a mixture of phthalimidoacetaldehyde diethyl acetal (3.5 g, 13.3 mmol) and cis,cis-9,12-octadecadien-1-ol (10.6 g, 39.9 mmol) was added pyridinium p-toluenesulfonate (0.167 g, 0.665 mmol) and heated to 105° C. After 48 h, the reaction was diluted in 300 ml of dichloromethane. The organic was washed by 100 ml of saturated sodium bicarbonate solution twice and brine (100 ml). The organic layer was dried over sodium sulfate, filtered and concentrated. The residue was purified by silica gel chromatography (0% ethyl acetate/hexane →20% ethyl acetate/hexane) to give the title compound (7.6 g). MS 726.6 (M+Na).

2,2-bis[(9Z,12Z)-octadeca-9,12-dien-1-yloxy]ethanamine (Compound 6)

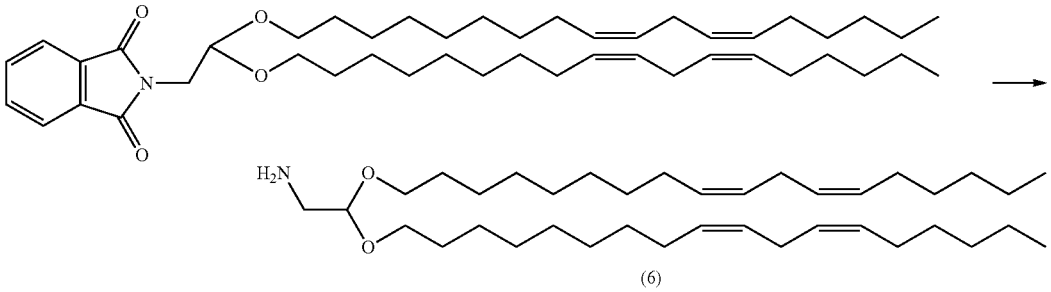

(6)

To solution of 2-{2,2-bis[(9Z,12Z)-octadeca-9,12-dien-1-yloxy]ethyl}-1H-isoindole-1,3(2H)-dione in benzene (40 ml) was added 6.3 ml of methylhydrazine and heated to 70° C. After 5 h, the reaction was filtrated and the solution was diluted in 200 ml of dichloromethane. The organic was washed by 100 ml of saturated sodium bicarbonate solution twice and brine (100 ml). The organic layer was dried over sodium sulfate, filtered and concentrated. The residue was purified by silica gel chromatography (1% MeOH/dichloromethane→15% MeOH/dichloromethane) to give the title compound (5.3 g). HRMS 574.5558 (M+1). $^1$H NMR δ (ppm) (CHCl$_3$-d): 5.40-5.29 (8 H, m), 4.39 (1 H, t, J=5.13 Hz), 3.62 (2 H, dt, J=9.36, 6.65 Hz), 3.45 (2 H, dt, J=9.36, 6.67 Hz), 2.77 (6 H, t, J=5.85 Hz), 2.05 (8 H, q, J=7.05 Hz), 1.62-1.54 (6 H, m), 1.50-1.14 (32 H, m), 0.89 (6 H, t, J=6.74 Hz).

(2R)-2-{bis[(9Z,12Z)-octadeca-9,12-dien-1-yloxy]methyl}pyrrolidine (Compound 8)

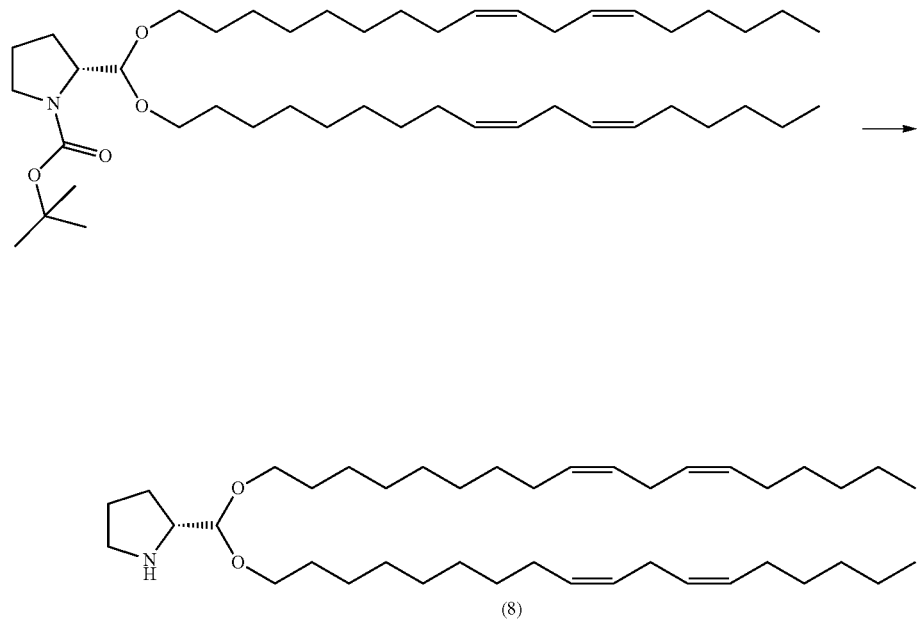

(8)

To a mixture of (R)—N-Boc-prolinal (4.9 g, 24.6 mmol) and cis,cis-9,12-octadecadien-1-ol (16.4 g, 61.5 mmol) was added pyridinium p-toluenesulfonate (0.309 g, 1.23 mmol) and heated to 105° C. After 72 h, the reaction was diluted in 300 ml of THF and cooled to 0° C. Gaseous HCl was bubbled into the THF solution for 3 minutes at 0° C. The reaction was stirred from 0° C. to ambient temperature for 5 h. The solvent was evaporated and reaction was redissolved by 300 ml dichloromethane. The organic was washed by 100 ml of saturated sodium bicarbonate solution twice and brine (100 ml). The organic layer was dried over sodium sulfate, filtered and concentrated. The residue was purified by silica gel chromatography (1% MeOH/dichloromethane→12% MeOH/dichloromethane) to give the title compound (8.2 g). MS 614.9 (M+1). HRMS 614.5873 (M+1). $^1$H NMR δ (ppm) (CHCl$_3$-d): 5.39-5.30 (8 H, m), 4.25 (1 H, d, J=6.83 Hz), 3.68-3.58 (2 H, m), 3.48 (2 H, p, J=7.71 Hz), 3.23 (1 H, q, J=7.14 Hz), 3.02-2.95 (1 H, m), 2.90-2.84 (1 H, m), 2.77 (4 H, t, J=6.82 Hz), 2.16-1.96 (8 H, m), 1.89-1.80 (1 H, m), 1.80-1.68 (2 H, m), 1.62-1.52 (5 H, m), 1.45-1.20 (32 H, m), 0.99-0.76 (6 H, m).

(2R)-2-{bis[(9Z,12Z)-octadeca-9,12-dien-1-yloxy]methyl}-1-methylpyrrolidine (Compound 9)

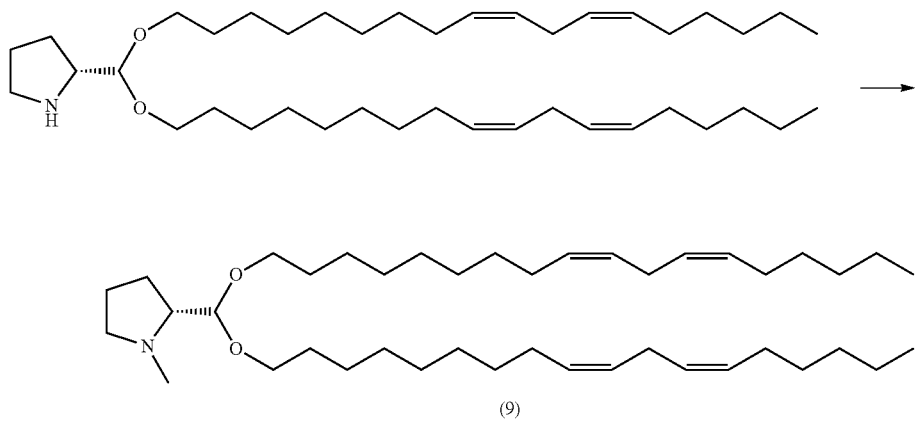

(9)

To 8 ml THF solution of (2R)-2-{bis[(9Z,12Z)-octadeca-9,12-dien-1-yloxy]methyl}pyrrolidine (Compound 8) (2.15 g, 3.50 mmol) was added 37% formaldehyde aqueous solution (2.61 ml, 35 mmol), acetic acid (0.401 ml, 7.00 mmol) and 8 M borane-pyridine complex (1.09 ml, 8.75 mmol) and stirred at ambient temperature. After 4 h, the reaction was diluted in 100 ml of dichloromethane. The organic was washed by 50 ml of saturated sodium bicarbonate solution twice and brine (50 ml). The organic layer was dried over sodium sulfate, filtered and concentrated. The residue was purified by silica gel chromatography (0% MeOH/dichloromethane→12% MeOH/dichloromethane) to give the title compound (1.05 g). MS 628.9 (M+1). HRMS 628.6039 (M+1). $^1$H NMR δ (ppm) (CHCl$_3$-d): 5.40-5.31 (8 H, m), 4.29 (1H, d, J=6.40 Hz), 3.65 (1 H, dt, J=9.22, 6.67 Hz), 3.58-3.46 (4 H, m), 3.05 (1 H, t, J=7.41 Hz), 2.77 (4 H, t, J=6.71 Hz), 2.45 (4 H,), 2.28-2.20 (1 H, m), 2.07-2.01 (8 H, m), 1.87 (1 H, t, J=9.78 Hz), 1.80-1.64 (2H, m), 1.63-1.52 (4 H, m), 1.45-1.20 (32 H, m), 0.89 (6 H, t, J=6.58 Hz).

2-[(2R)-2-{bis[(9Z,12Z)-octadeca-9,12-dien-1-yloxy]methyl}pyrrolidin-1-yl]ethanol (Compound 10)

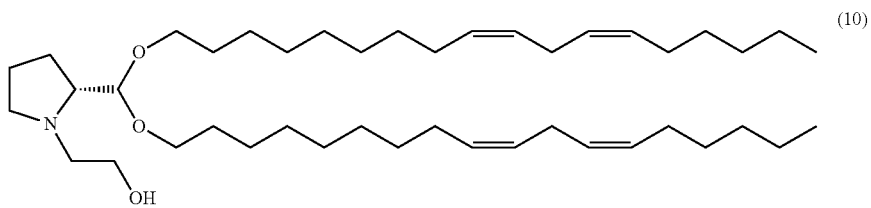 [SMILES: CCCCC/C=C\C/C=C\CCCCCCCCOC(OCCCCCCCC/C=C\C/C=C\CCCCC)[C@H]1CCCN1CCO]

(10)

Compound 10 can be prepared according to General Scheme 3 above.

MS 658.8 (M+1). HRMS 658.6156 (M+1). $^1$H NMR δ (ppm) (CHCl$_3$-d): 5.41-5.29 (8 H, m), 4.25 (1 H, d, J=6.26 Hz), 3.67-3.53 (4 H, m), 3.52-3.43 (2 H, m), 3.18-3.05 (2 H, m), 2.95-2.70 (5 H, m), 2.59 (1 H, dt, J=12.59, 3.75 Hz), 2.36 (1 H, q, J=8.37 Hz), 2.05 (8 H, q, J=7.11 Hz), 1.87-1.71 (4 H, m), 1.64-1.45 (4 H, m), 1.42-1.22 (32 H, m), 0.89 (6 H, t, J=6.73 Hz).

(2S)-1,1-bis[(9Z,12Z)-octadeca-9,12-dien-1-yloxy]propan-2-amine (Compound 11)

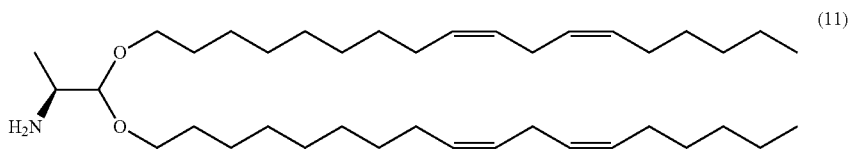 [SMILES: CCCCC/C=C\C/C=C\CCCCCCCCOC(OCCCCCCCC/C=C\C/C=C\CCCCC)[C@H](C)N]

(11)

Compound 11 can be prepared according to General Scheme 3 above.

HRMS 588.5731 (M+1). $^1$H NMR δ (ppm) (CHCl$_3$-d): 5.39-5.30 (8 H, m), 4.08 (1 H, d, J=5.87 Hz), 3.64 (2 H, ddt, J=22.87, 9.24, 6.57 Hz), 3.45 (2 H, dt, J=9.23, 6.72 Hz), 2.97 (1 H, t, J=6.30 Hz), 2.77 (4 H, t, J=6.49 Hz), 2.05 (8 H, q, J=6.91 Hz), 1.65-1.5 (4 H, m), 1.45-1.20 (32 H, m), 1.07 (3 H, d, J=6.51 Hz), 0.89 (6 H, t, J=6.76 Hz).

2-(1-hydroxy-2-methylpropan-2-yl)-1H-isoindole-1,3(2H)-dione (Compound 12)

To 12 ml DMF solution of 2-amino-2-methylpropan-1-ol (1.70 g, 19.1 mmol) was added phthalic anhydride (3.11 g, 21.0 mmol) and triethyl amine (5.85 ml, 42 mmol). The mixture was microwaved at 145° C. for 2 h. After evaporation of solvent, the residue was purified by silica gel chromatography (0% MeOH/dichloromethane→5% MeOH/dichloromethane) to give the title compound (1.9 g). MS 220.3 (M+1).

2-(1,3-dioxo-1,3-dihydro-2H-isoindol-2-yl)-2-methylpropanal (Compound 13)

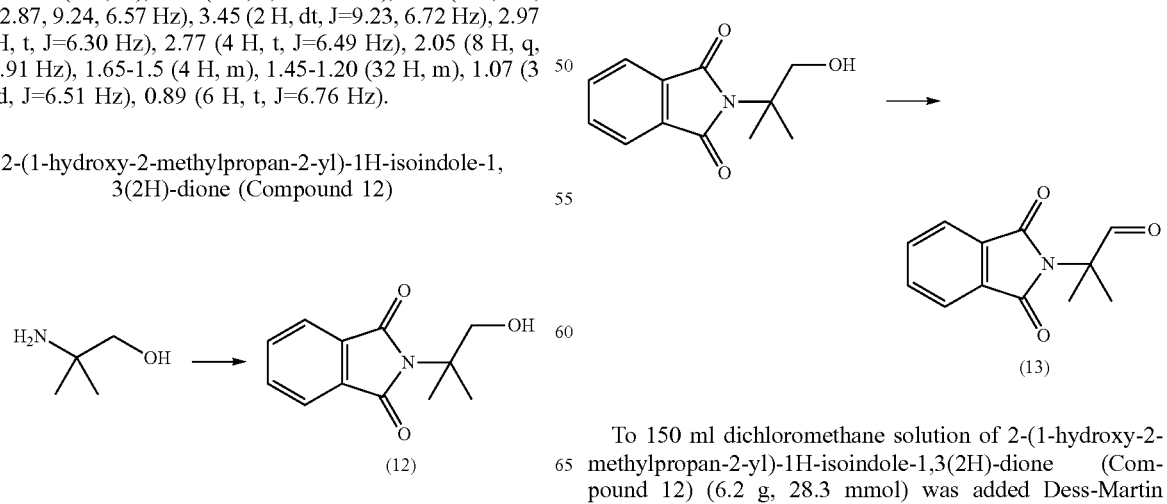

(13)

To 150 ml dichloromethane solution of 2-(1-hydroxy-2-methylpropan-2-yl)-1H-isoindole-1,3(2H)-dione (Compound 12) (6.2 g, 28.3 mmol) was added Dess-Martin periodinane (14.4 g, 33.9 mmol) and stirred at ambient temperature for 16 h. The reaction was diluted in 200 ml of dichloromethane. The organic was washed by 100 ml 1 M sodium thiosulfate aqueous solution twice, saturated sodium bicarbonate solution twice and brine (100 ml). The organic layer was dried over sodium sulfate, filtered and concentrated. The residue was purified by silica gel chromatography (0% MeOH/dichloromethane→5% MeOH/dichloromethane) to give the title compound (5.6 g). MS 218.3 (M+1).

2-{2-methyl-1,1-bis[(9Z,12Z)-octadeca-9,12-dien-1-yloxy]propan-2-yl}-1H-isoindole-1,3(2H)-dione
(Compound 14)

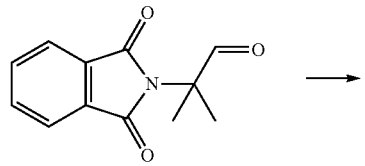

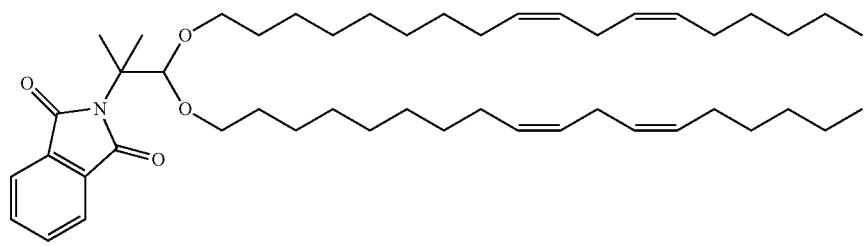

(14)

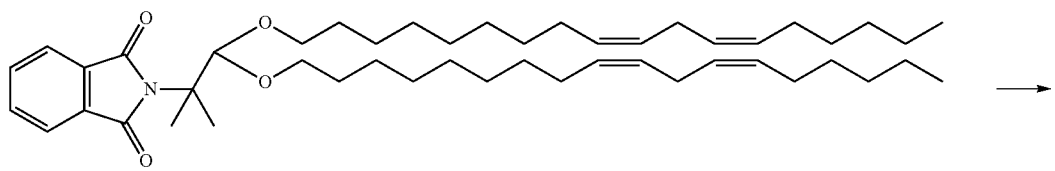

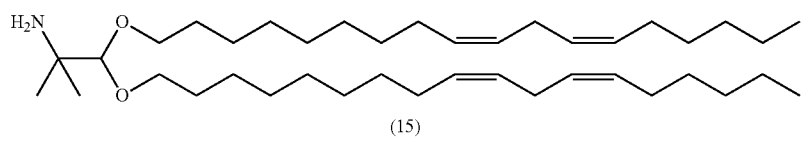

(15)

To a mixture of 2-(1,3-dioxo-1,3-dihydro-2H-isoindol-2-yl)-2-methylpropanal (4.78 g, 22.0 mmol) and cis,cis-9,12-octadecadien-1-ol (17.6 g, 66.0 mmol) was added pyridinium p-toluenesulfonate (0.553 g, 0.220 mmol) and heated to 120° C. After 48 h, the reaction was diluted in 300 ml of dichloromethane. The organic was washed by 100 ml of saturated sodium bicarbonate solution twice and brine (100 ml). The organic layer was dried over sodium sulfate, filtered and concentrated. The residue was purified by silica gel chromatography (0% ethyl acetate/hexane→20% ethyl acetate/hexane) to give the title compound (9.1 g). MS 754.9 (M+Na).

2-methyl-1,1-bis[(9Z,12Z)-octadeca-9,12-dien-1-yloxy]propan-2-amine (Compound 15)

To a 140 ml benzene solution of 2-{2-methyl-1,1-bis[(9Z,12Z)-octadeca-9,12-dien-1-yloxy]propan-2-yl}-1H-isoindole-1,3(2H)-dione (Compound 14) (7.0 g, 9.56 mmol) was added methyl hydrazine (3.52 g, 76 mmol) and heated to 70° C. After 5 h, the reaction was filtrated and the solution was diluted with 200 ml of dichloromethane. The organic was washed by 100 ml of saturated sodium bicarbonate solution twice and brine (100 ml). The organic layer was dried over sodium sulfate, filtered and concentrated. The residue was purified by silica gel chromatography (0.5% MeOH/dichloromethane→10% MeOH/dichloromethane) to give the title compound (3.5 g). MS 602.8 (M+1). HRMS 602.5877 (M+1). $^1$H NMR δ (ppm) (CHCl$_3$-d): 5.41-5.30 (8 H, m), 4.00 (1 H, s), 3.78 (2 H, dt, J=9.04, 6.44 Hz), 3.47 (2 H, dt, J=9.08, 6.78 Hz), 2.77 (4 H, t, J=6.73 Hz), 2.05 (8 H, q, J=7.00 Hz), 1.63-1.45 (4H, m), 1.42-1.20 (32 H, m), 1.06 (6 H, s), 0.89 (6 H, t, J=6.67 Hz).

9H-fluoren-9-ylmethyl 4,4-diethoxypiperidine-1-carboxylate (Compound 16)

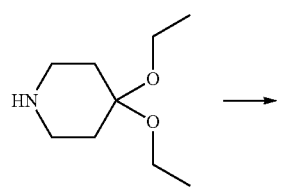

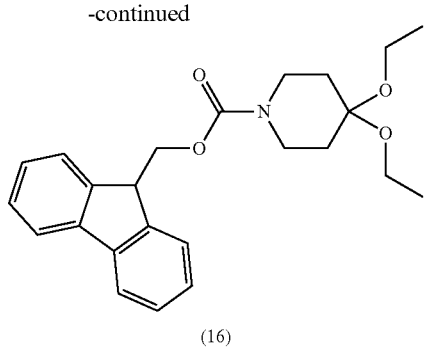

(16)

To 40 ml ethanol solution of 1-benzyl-4,4-diethoxypiperidine (3.3 g, 12.5 mmol) was added 0.4 g palladium hydroxide on carbon (20 wt %). The reaction was hydrogenated under 45 psi hydrogen. After 16 h, the reaction was filtrated and evaporated of solvent. The residue was stirred with 1-{[(9H-fluoren-9-ylmethoxy)carbonyl]oxy}pyrrolidine-2,5-dione (5.14 g, 15.2 mmol) and sodium bicarbonate (5.33 g, 63.5 mmol) in 180 ml of 10:1 dioxane/water solvent. After 16 h, the reaction was diluted with 400 ml of dichloromethane. The organic was washed by 300 ml of saturated sodium bicarbonate solution twice and brine (300 ml). The organic layer was dried over sodium sulfate, filtered and concentrated. The residue was purified by silica gel chromatography (0% ethyl acetate/hexane→60% ethyl acetate/hexane) to give the title compound (4.8 g). MS 418.4 (M+Na).

9H-fluoren-9-ylmethyl 4,4-bis[(9Z,12Z)-octadeca-9,12-dien-1-yloxy]piperidine-1-carboxylate (Compound 17)

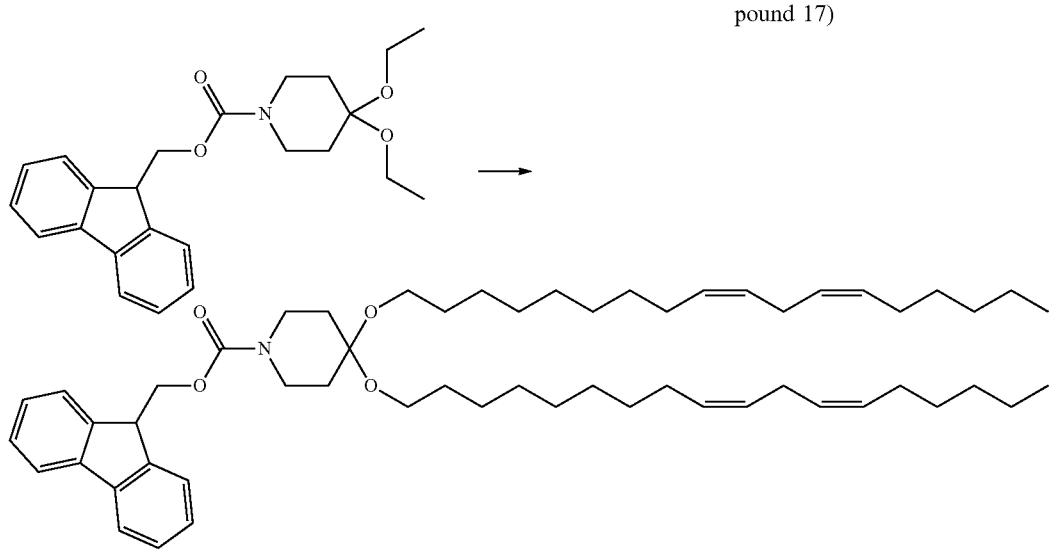

(17)

To 120 ml toluene solution of 9H-fluoren-9-ylmethyl 4,4-diethoxypiperidine-1-carboxylate (4.8 g, 12.1 mmol) and cis,cis-9,12-octadecadien-1-ol (9.70 g, 36.4 mmol) was added pyridinium p-toluenesulfonate (0.305 g, 1.21 mmol) and heated to 100° C. After 48 h, the reaction was diluted in 300 ml of dichloromethane. The organic was washed by 100 ml of saturated sodium bicarbonate solution twice and brine (100 ml). The organic layer was dried over sodium sulfate, filtered and concentrated. The residue was purified by silica gel chromatography (0% ethyl acetate/hexane→20% ethyl acetate/hexane) to give the title compound (7.5 g). $^1$H NMR δ (ppm) (CHCl$_3$-d): 7.76 (2 H, d, J=7.60 Hz), 7.58 (2 H, d, J=7.53 Hz), 7.40 (2 H, t, J=7.49 Hz), 7.32 (2 H, d, J=7.56 Hz), 5.42-5.31 (8 H, m), 4.41 (2 H, d, J=6.92 Hz), 4.25 (1 H, t, J=6.93 Hz), 3.48 (4 H, s, b), 3.39 (4 H, t, J=6.78 Hz), 2.78 (4 H, t, J=6.86 Hz), 2.05 (8 H, d, J=8.02 Hz), 1.72 (4 H, s, b), 1.60-1.50 (4 H, m), 1.42-1.20 (32 H, m), 0.89 (6 H, t, J=6.61 Hz).

4,4-bis[(9Z,12Z)-octadeca-9,12-dien-1-yloxy]piperidine (Compound 18)

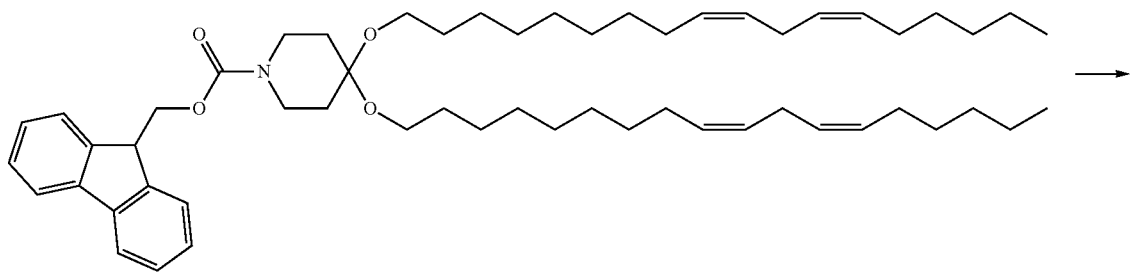

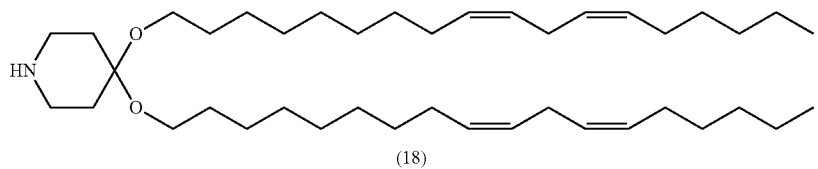

(18)

To 150 ml dichloromethane solution of 9H-fluoren-9-ylmethyl 4,4-bis[(9Z,12Z)-octadeca-9,12-dien-1-yloxy]piperidine-1-carboxylate (Compound 17) (7.3 g, 8.73 mmol) was added piperidine (7.43 g, 87 mmol). After 16 h at ambient temperature, the reaction was filtrated and the solution was diluted with 300 ml of dichloromethane. The organic was washed by 150 ml of saturated sodium bicarbonate solution twice and brine (150 ml). The organic layer was dried over sodium sulfate, filtered and concentrated. The residue was purified by silica gel chromatography (0% MeOH/dichloromethane→12% MeOH/dichloromethane) to give the title compound (3.9 g). MS 614.7 (M+1). HRMS 614.5863 (M+1). $^1$H NMR δ (ppm) (CHCl$_3$-d): 5.40-5.31 (8 H, m), 3.38 (4 H, t, J=6.76 Hz), 2.84 (4 H, t, J=5.27 Hz), 2.77 (4 H, t, J=6.81 Hz), 2.05 (8 H, q, J=7.03 Hz), 1.71 (4 H, s, b), 1.56-1.49 (4 H, m), 1.42-1.2 (32 H, m), 0.89 (6 H, t, J=6.74 Hz).

3,3-bis[(9Z,12Z)-octadeca-9,12-dien-1-yloxy]pyrrolidine (Compound 19)

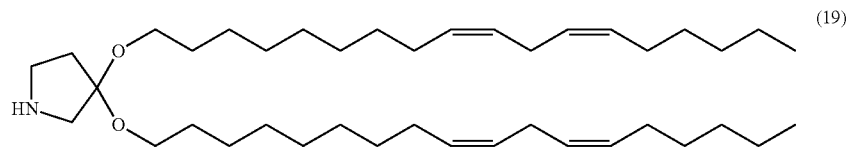 [SMILES: CCCCC/C=C\C/C=C\CCCCCCCCOC1(OCCCCCCCC/C=C\C/C=C\CCCCC)CCNC1]

Compound 19 can be prepared according to General Scheme 3 above. MS 600.8 (M+1). HRMS 600.5711 (M+1). $^1$H NMR δ (ppm) (CHCl$_3$-d): 5.41-5.31 (8H, m), 3.41 (4 H, t, J=6.80 Hz), 3.10 (2 H, t, J=7.30 Hz), 2.98 (2 H, s), 2.77 (4 H, t, J=6.82 Hz), 2.05 (8H, q, J=7.04 Hz), 1.95 (2 H, t, J=7.30 Hz), 1.55 (4 H, t, J=7.01 Hz), 1.51-1.20 (32 H, m), 0.89 (6 H, t, J=6.76 Hz).

N,N-dimethyl-3,3-bis[(9Z,12Z)-octadeca-9,12-dien-1-yloxy]propan-1-amine (Compound 20)

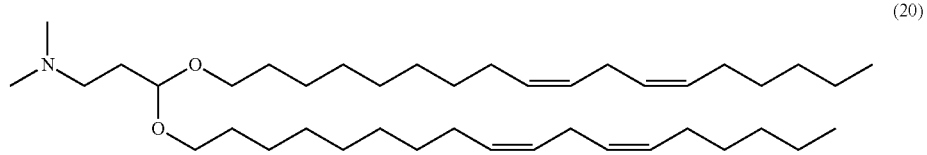 [SMILES: CCCCC/C=C\C/C=C\CCCCCCCCOC(CCN(C)C)OCCCCCCCC/C=C\C/C=C\CCCCC]

Compound 20 was prepared according to General Scheme 6 above and with chemistry as described for Compound 2. $^1$H NMR δ (ppm) (CHCl$_3$-d): 5.41-5.30 (8 H, m), 4.54 (1 H, t, J=5.7 Hz), 3.60-3.55 (2 H, m), 3.43-3.39 (2 H, m), 2.79-2.76 (2 H, m), 2.34-2.31 (2 H, m), 2.22 (6 H, s), 2.07-2.02 (8 H, m), 1.80-1.76 (2 H, m), 1.58-1.53 (4 H, m), 1.39-1.25 (32 H, m), 0.91-0.87 (6 H, m).

1-{3,3-bis[(9Z,12Z)-octadeca-9,12-dien-1-yloxy]propyl}pyrrolidine (Compound 21)

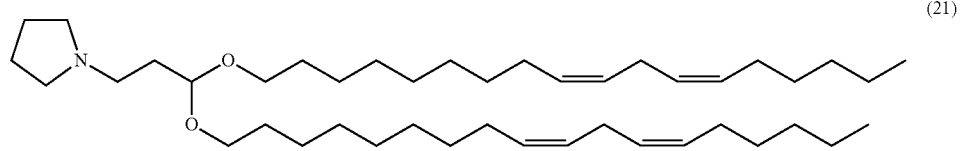 [SMILES: CCCCC/C=C\C/C=C\CCCCCCCCOC(CCN1CCCC1)OCCCCCCCC/C=C\C/C=C\CCCCC]

Compound 21 was prepared according to General Scheme 6 above and with chemistry as described for Compound 2. HRMS (M+1) calc'd: 642.6111, found: 642.6169.

3,3-bis[(9Z,12Z)-octadeca-9,12-dien-1-yloxy]propan-1-amine (Compound 22)

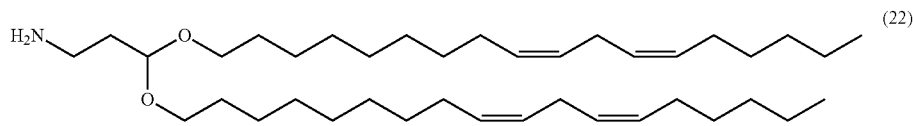 [SMILES: CCCCC/C=C\C/C=C\CCCCCCCCOC(CCN)OCCCCCCCC/C=C\C/C=C\CCCCC]

Compound 22 was prepared according to General Scheme 7 above and with chemistry as described for compounds 2 and 6. HRMS (M+1) calc'd: 588.5641, found: 588.5712.

N,N-dimethyl-2,2-bis[(9Z)-octadec-9-en-1-yloxy]ethanamine (Compound 23)

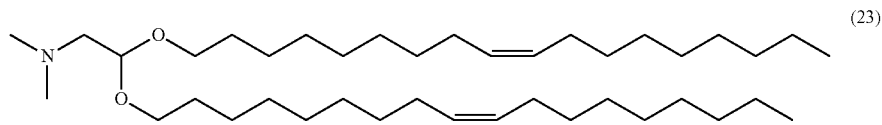 [SMILES: CCCCCCCC/C=C\CCCCCCCCOC(CN(C)C)OCCCCCCCC/C=C\CCCCCCCC]

Compound 23 was prepared according to General Scheme 1 with chemistry as described for compound 2. HRMS (M+1) calc'd: 606.6111, found: 606.6184.

tert-butyl 1-(1,3-dioxo-1,3-dihydro-2H-isoindol-2-yl)cyclopropanecarboxylate (Compound 24)

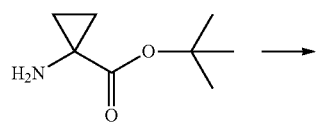

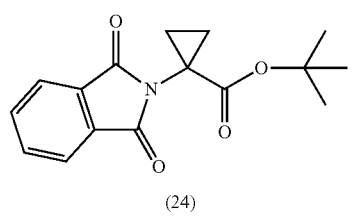

To 45 mL DMF solution of tert-butyl 1-aminocyclopropanecarboxylate (1.8 g, 11.5 mmol) was added phthalic anhydride (2.04 g, 13.7 mmol) and diisopropylethylamine (10.0 mL, 57.2 mmol). After heating at 160° C. for 16 h, the reaction was diluted by 150 ml of dichloromethane. The organic was washed by 1×100 mL of saturated NaHCO$_3$ solution, water and brine, respectively. The organic was dried over Na$_2$SO$_4$, filtrated and concentrated. The residue was purified by silica gel chromatography (0% EtOAC/hexane→50% EtOAc/hexane) give title compound (2.80 g). MS 310.2 (M+Na).

1-(1,3-dioxo-1,3-dihydro-2H-isoindol-2-yl)-N-methoxy-N-methylcyclopropanecarboxamide (Compound 25)

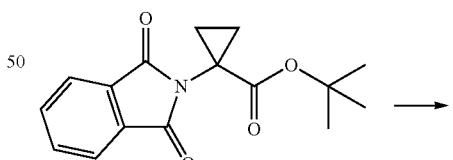

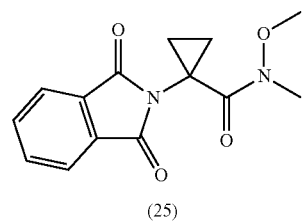

To a 45 mL dichloromethane solution of tort-butyl 1-(1,3-dioxo-1,3-dihydro-2H-isoindol-2-yl)cyclopropanecarboxylate (2.8 g, 9.75 mmol) was added 5 mL of TFA. After 16 h at ambient temperature, the reaction was concentrated. The residue was retaken by 150 ml of dichloromethane and 1×100 mL of 1N HCl solution, water and brine. Evaporation of solvent gave 1-(1,3-dioxo-1,3-dihydro-2H-isoindol-2-yl) cyclopropanecarboxylic acid (2.2 g). MS 254.1 (M+Na). 1-(1,3-dioxo-1,3-dihydro-2H-isoindol-2-yl)cyclopropanecarboxylic acid (2.2 g, 9.52 mmol) was dissolved in 50 mL of dichloromethane/DMF 4:1 solvent. To this, N,O-dimethylhydroxylamine hydrochloride (1.39 g, 14.3 mmol) was added in followed by EDC (4.01 g, 20.9 mmol), HOBt (1.60 g, 10.5 mmol) and diisopropylethylamine (6.65 mL, 38.1 mmol). After 16 h at ambient temperature, the reaction was concentrated and the residue was retaken by 150 mL of dichloromethane, washed by 1×100 mL of saturated NaHCO$_3$ solution, water and brine. The organic was dried over Na$_2$SO$_4$, filtrated and concentrated. The residue was purified by silica gel chromatography (0% EtOAC/hexane→65% EtOAc/hexane) give title compound (2.45 g). MS 275.2 (M+1).

1-(1,3-dioxo-1,3-dihydro-2H-isoindol-2-yl)cyclopropanecarbaldehyde (Compound 26)

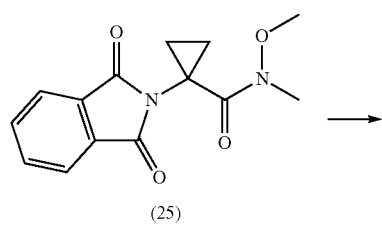

(25)

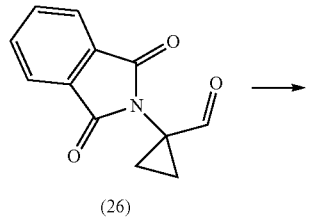

(26)

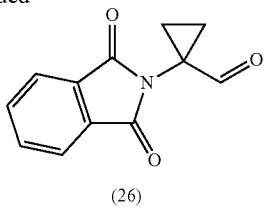

(26)

To a 100 mL THF solution of 1-(1,3-dioxo-1,3-dihydro-2H-isoindol-2-yl)-N-methoxy-N-methylcyclopropanecarboxamide (2.45 g, 8.93 mmol) at −78° C. was added 1 M DiBAL solution in Toluene (19.65 mL). After 3 h at −78° C., the reaction was quenched with 30 mL of saturated NH$_4$Cl solution. The solution was concentrated and the residue was retaken by 200 mL of EtOAc. The organic was washed by 1×100 mL of 0.5 N Rochelle's salt, saturated NaHCO$_3$ solution, water and brine. The organic was dried over Na$_2$SO$_4$, filtrated and concentrated. The residue was purified by silica gel chromatography (5% EtOAC/hexane→75% EtOAc/hexane) to give title compound (1.32 g). MS 216.1 (M+1).

2-(1-{bis[(9Z,12Z)-octadeca-9,12-dien-1-yloxy] methyl}cyclopropyl)-1H-isoindole-1,3(2H)-dione (Compound 27)

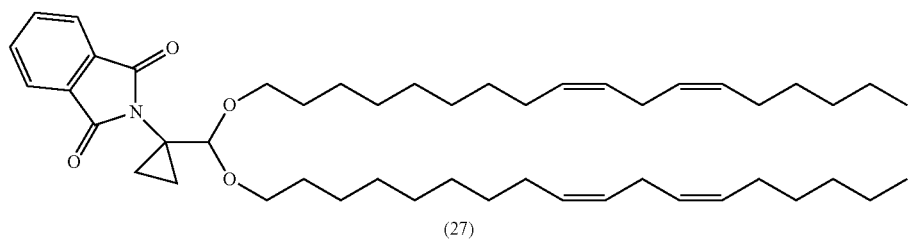

(27)

To a 10 mL Toluene solution of 1-(1,3-dioxo-1,3-dihydro-2H-isoindol-2-yl)cyclopropanecarbaldehyde (1.3 g, 6.04 mmol) and (9Z,12Z)-octadeca-9,12-dien-1-ol (5.68 mL, 18.1 mmol) was added camphorsulfonic acid (0.14 g, 0.604 mmol). The reaction was heated at 110° C. for 36 hours. The reaction was purified directly by silica gel chromatography (0% EtOAC/hexane→16% EtOAc/hexane) to give title compound (2.5 g). MS 730.9 (M+1).

1-{bis[(9Z,12Z)-octadeca-9,12-dien-1-yloxy]methyl}cyclopropanamine (Compound 28)

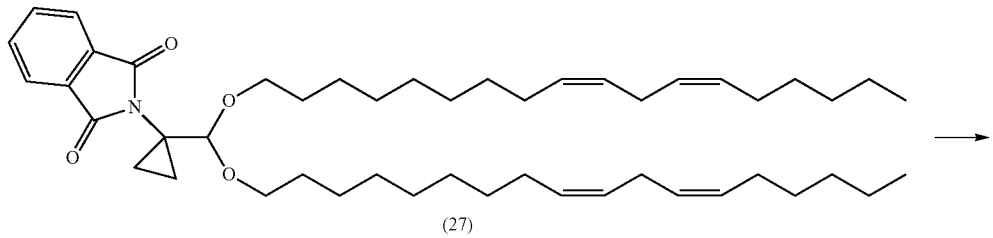

(27)

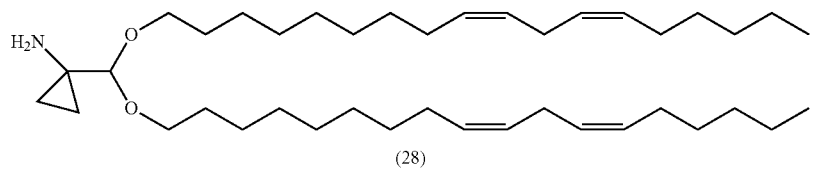

(28)

To 100 mL solution of 2-(1-{bis[(9Z,12Z)-octadeca-9,12-dien-1-yloxy]methyl}cyclopropyl)-1H-isoindole-1,3(2H)-dione (2.4 g, 3.29 mmol) was added methylhydrazine (1.73 mL, 32.9 mmol). The reaction was refluxed for 10 hours. The solvent was evaporated and the residue was retaken by 200 mL of hexane and filtrated. The solution was washed by 2×100 mL of NaHCO$_3$ solution, water and brine, respectively. The organic was dried over Na$_2$SO$_4$, filtrated and concentrated. The residue was purified by reverse-phase HPLC (70%-100% CH3CN/water) to give the title compound (1.45 g). MS 600.9 (M+1). HRMS 600.5719 (M+1). $^1$H NMR δ (ppm) (CHCl$_3$-d): 5.41-5.30 (8 H, m), 4.07 (1 H, s), 3.64-3.60 (2 H, m), 3.48-3.43 (2 H, m), 2.79-2.76 (4 H, m), 2.07-2.02 (8 H, m), 1.61-1.55 (4 H, m), 1.39-1.26 (32 H, m), 0.91-0.87 (6 H, m), 0.62-0.55 (4H, m).

(6Z,9Z)-18-(2-bromo-1-methoxyethoxy)octadeca-6,9-diene (Compound 29)

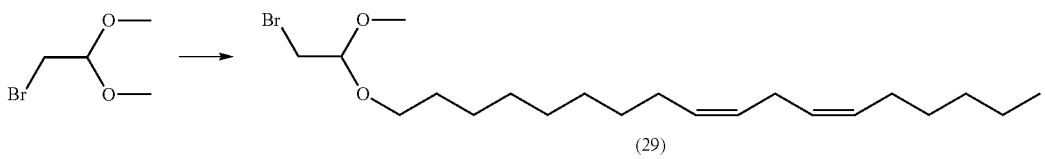

(29)

To 200 ml dichloroethane solution of 2-bromo-1,1-dimethoxyethane (5.0 g, 29.0 mmol) under an ice bath was added 2,6-lutidine (11.33 mL, 98 mmol) and TMSOTf (11.8 mL, 65.1 mmol). The reaction stirred under the ice bath for one hour. After which, (9Z,12Z)-octadeca-9,12-dien-1-ol (27.8 mL, 89 mmol) was added in and the reaction was stirred from 0° C. to 20° C. for 16 hours. The reaction was diluted with 300 mL dichloromethane and washed by 200 mL of NaHCO$_3$ solution, water, brine, respectively. The organic was dried over Na$_2$SO$_4$, filtrated and purified by silica gel chromatography (0% ethyl acetate/hexane→10% ethyl acetate/hexane) to give (6Z,9Z)-18-(2-bromo-1-methoxyethoxy)octadeca-6,9-diene (Compound 29) (11.3 g).

(6Z,9Z)-18-[2-bromo-1-(octyloxy)ethoxy]octadeca-6,9-diene (Compound 30)

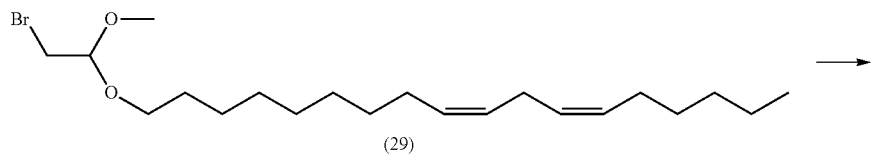

(29)

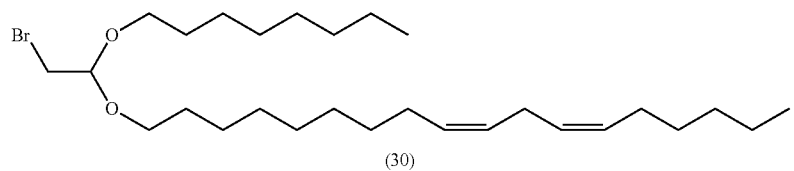

(30)

To 50 ml dichloromethane solution of (6Z,9Z)-18-(2-bromo-1-methoxyethoxy)octadeca-6,9-diene (Compound 29) (4.0 g, 9.91 mmol) under an ice bath was added collidine (4.32 mL, 32.7 mmol) and TMSOTf (4.12 mL, 22.8 mmol). The reaction stirred under the ice bath for 3 hours. After which, 1-octanol (7.81 mL, 49.6 mmol) was added in and the reaction was stirred from 0° C. to 20° C. for 16 hours. The reaction was diluted with 200 mL dichloromethane and washed by 100 mL of NaHCO$_3$ solution, water, brine. The organic was dried over Na$_2$SO$_4$, filtrated and purified by silica gel chromatography (0% dichloromethane/hexane→50% dichloromethane/hexane) to give title compound (3.6 g). MS 523.6 (M+Na).

N,N-dimethyl-2-[(9Z,12Z)-octadeca-9,12-dien-1-yloxy]-2-(octyloxy)ethanamine (Compound 31)

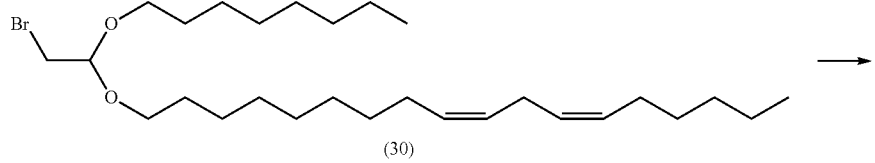

(30)

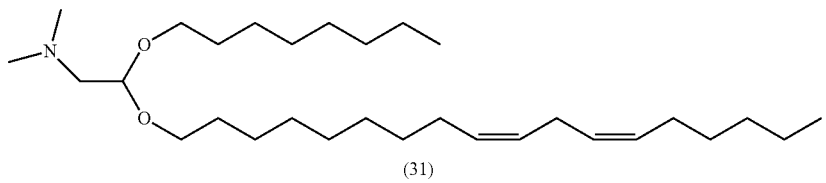

(31)

To (6Z,9Z)-18-[2-bromo-1-(octyloxy)ethoxy]octadeca-6,9-diene (Compound 30) (1.76 g, 3.51 mmol) in a microwave tube was added 40% dimethylamine (4.44 mL) aqueous solution. The reaction was heated to 160° C. for 30 minutes under microwave. After which, the reaction was diluted with 150 mL of Hexane, and washed by 2×100 mL of NaHCO$_3$ solution, water and brine, respectively. The organic was dried over Na$_2$SO$_4$ and filtrated. Evaporation of solvent to dryness gave the title compound (1.60 g). MS 466.4 (M+1). HRMS 466.4627 (M+1). $^1$H NMR δ (ppm) (CHCl$_3$-d): 5.39-5.31 (4 H, m), 4.58 (1 H, t, J=5.3 Hz), 3.61-3.56 (2 H, m), 3.48-3.43 (2 H, m), 2.77 (2 H, t, J=6.7 Hz), 2.46 (2 H, d, J=5.3 Hz), 2.29 (6 H, s), 2.07-2.02 (4 H, m), 1.60-1.55 (4 H, m), 1.37-1.27 (26 H, m), 0.90-0.86 (6 H, m).

2-(decyloxy)-N,N-dimethyl-2-[(9Z,12Z)-octadeca-9,12-dien-1-yloxy]ethanamine (Compound 32)

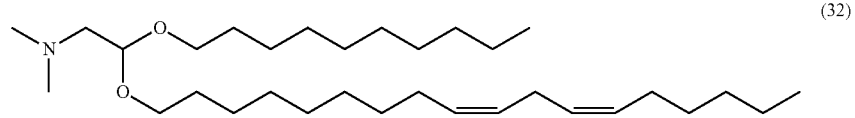 [SMILES: CCCCC/C=C\C/C=C\CCCCCCCCOC(CN(C)C)OCCCCCCCCCC]

(32)

Compound 32 was prepared according to General Scheme 9 as described for Compound 31. HRMS (M+1) calc'd: 494.4859; found: 494.4922.

2-[(8Z)-dodec-8-en-1-yloxy]-N,N-dimethyl-2-[(9Z,12Z)-octadeca-9,12-dien-1-yloxy]ethanamine (Compound 33)

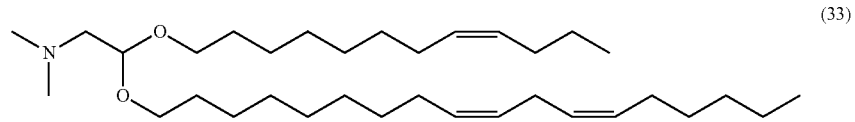 [SMILES: CCC/C=C\CCCCCCCOC(CN(C)C)OCCCCCCCC/C=C\C/C=C\CCCCC]

(33)

Compound 33 was prepared according to General Scheme 9 as described for Compound 31. $^1$H NMR δ (ppm) (CHCl$_3$-d): 5.39-5.32 (6 H, m), 4.58 (1 H, t, J=5.3 Hz), 3.60-3.56 (2 H, m), 3.48-3.43 (2 H, m), 2.77 (2 H, t, J=6.6 Hz), 2.46 (2 H, d, J=5.4 Hz), 2.29 (6 H, s), 2.06-1.99 (8 H, m), 1.60-1.55 (6 H, m), 1.39-1.29 (24 H, m), 0.92-0.87 (6 H, m). HRMS (M+1) calc'd: 520.5015; found: 520.5073.

1-{2-[(8Z)-dodec-8-en-1-yloxy]-2-[(9Z,12Z)-octadeca-9,12-dien-1-yloxy]ethyl}pyrrolidine (Compound 34)

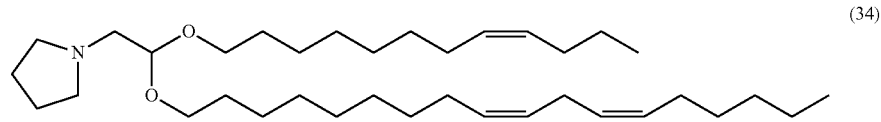 [SMILES: CCC/C=C\CCCCCCCOC(CN1CCCC1)OCCCCCCCC/C=C\C/C=C\CCCCC]

(34)

Compound 34 was prepared according to General Scheme 9 as described for Compound 31. HRMS (M+1) calc'd: 546.5172; found: 546.5235.

1-{2-[(9Z,12Z)-octadeca-9,12-dien-1-yloxy]-2-(octyloxy)ethyl}pyrrolidine (Compound 35)

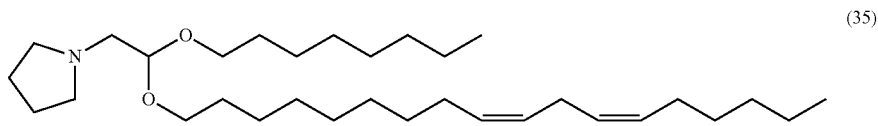 [SMILES: CCCCC/C=C\C/C=C\CCCCCCCCOC(CN1CCCC1)OCCCCCCCC]
(35)

Compound 35 was prepared according to General Scheme 9 as described for Compound 31. HRMS (M+1) calc'd: 492.4702; found: 492.4788.

[(2S)-1-{2-(decyloxy)-2-[(9Z,12Z)-octadeca-9,12-dien-1-yloxy]ethyl}pyrrolidin-2-yl]methanol (Compound 36)

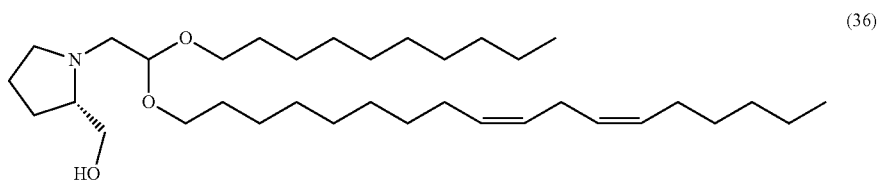 [SMILES: CCCCC/C=C\C/C=C\CCCCCCCCOC(CN1CCC[C@H]1CO)OCCCCCCCCCC]
(36)

Compound 36 was prepared according to General Scheme 9 as described for Compound 31. HRMS (M+1) calc'd: 550.5121; found: 550.5211.

1-{2-(decyloxy)-2-[(9Z,12Z)-octadeca-9,12-dien-1-yloxy]ethyl}piperidin-4-ol (Compound 37)

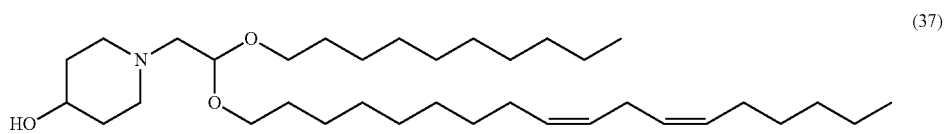 [SMILES: CCCCC/C=C\C/C=C\CCCCCCCCOC(CN1CCC(O)CC1)OCCCCCCCCCC]
(37)

Compound 37 was prepared according to General Scheme 9 as described for Compound 31. HRMS (M+1) calc'd: 550.5121; found: 550.5208.

N,N-dimethyl-3-[(9Z,12Z)-octadeca-9,12-dien-1-yloxy]-3-(octyloxy)propan-1-amine (Compound 38)

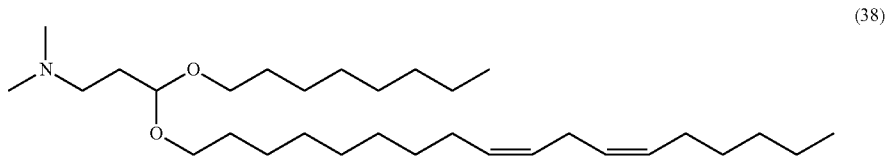 [SMILES: CCCCC/C=C\C/C=C\CCCCCCCCOC(CCN(C)C)OCCCCCCCC]
(38)

Compound 38 was prepared according to General Scheme 9 as described for Compound 31. HRMS (M+1) calc'd: 480.4702; found: 480.4763.

2-(heptyloxy)-N,N-dimethyl-2-[(9Z,12Z)-octadeca-9,12-dien-1-yloxy]ethanamine (Compound 39)

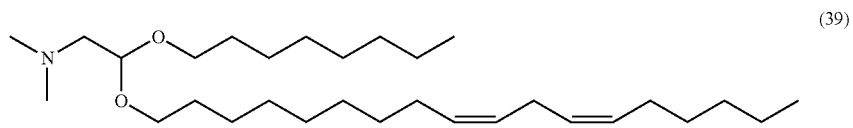 [SMILES: CCCCC/C=C\C/C=C\CCCCCCCCOC(CN(C)C)OCCCCCCCC]

(39)

Compound 39 was prepared according to General Scheme 9 as described for Compound 31. HRMS (M+1) calc'd: 452.4389; found: 452.446.

N,N-dimethyl-2-(nonyloxy)-2-[(9Z,12Z)-octadeca-9,12-dien-1-yloxy]ethanamine (Compound 40)

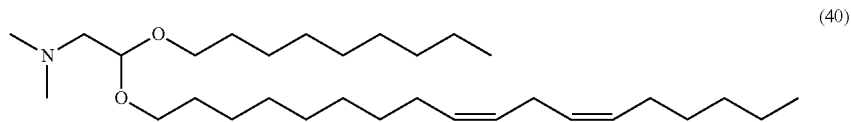

(40)

Compound 40 was prepared according to General Scheme 9 as described for Compound 31. HRMS (M+1) calc'd: 480.4702; found: 480.4772.

1-{3-[(9Z,12Z)-octadeca-9,12-dien-1-yloxy]-3-(octyloxy)propyl}pyrrolidine (Compound 41)

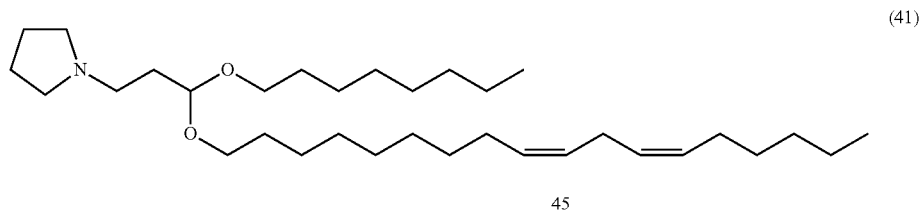

(41)

Compound 41 was prepared according to General Scheme 9 as described for Compound 31. HRMS (M+1) calc'd: 506.4859; found: 506.4929.

2-{2-ethoxy-2-[(9Z,12Z)-octadeca-9,12-dien-1-yloxy]ethyl}-1H-isoindole-1,3(2H)-dione (Compound 42)

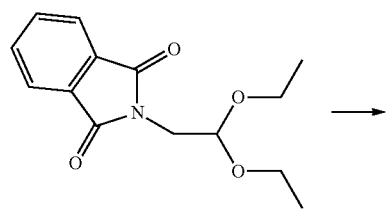

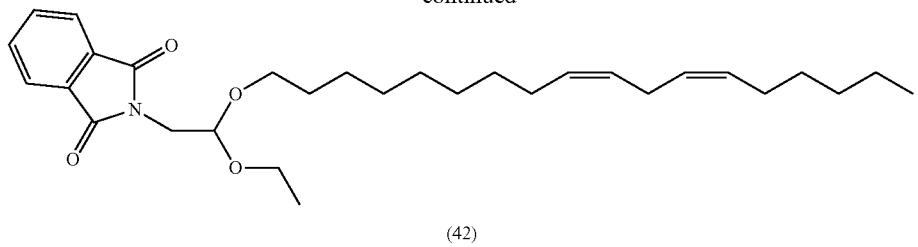

(42)

To 50 ml dichloromethane solution of 2-(2,2-diethoxyethyl)-1H-isoindole-1,3(2H)-dione (6.8 g, 25.8 mmol) under an ice bath was added 2,6-lutidine (9.89 mL, 85 mmol) and TMSOTf (10.3 mL, 56.8 mmol). The reaction stirred under the ice bath for one hour. After which, (9Z,12Z)-octadeca-9,12-dien-1-ol (24.3 mL, 77 mmol) was added in and the reaction was stirred from 0° C. to 20° C. for 16 hours. The reaction was diluted with 200 mL dichloromethane and washed by 100 mL of NaHCO$_3$ solution, water, brine. The organic was dried over Na$_2$SO$_4$, filtrated and purified by silica gel chromatography (0% ethyl acetate/hexane→18% ethyl acetate/hexane) to give title compound (12.1 g). MS 506.5 (M+Na).

2-{2-(hexyloxy)-2-[(9Z,12Z)-octadeca-9,12-dien-1-yloxy]ethyl}-1H-isoindole-1,3(2H)-dione (Compound 43)

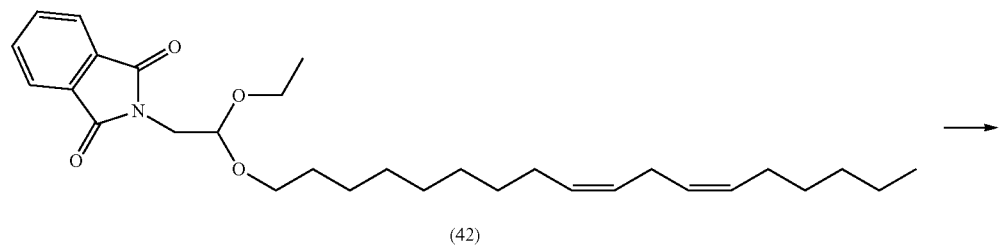

(42)

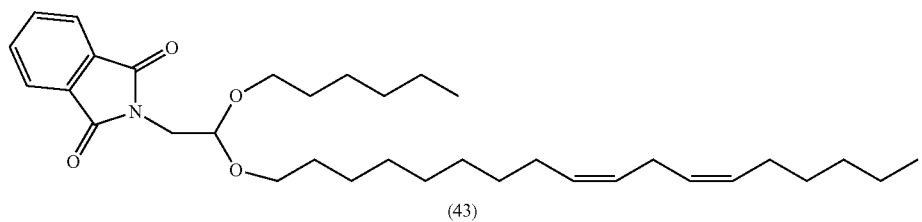

(43)

To 40 ml dichloroethane solution of 2-{2-ethoxy-2-[(9Z,12Z)-octadeca-9,12-dien-1-yloxy]ethyl}-1H-isoindole-1,3(2H)-dione (compound 42) (4.10 g, 8.48 mmol) under an ice bath was added 2,6-lutidine (3.25 mL, 28.0 mmol) and TMSOTf (3.37 mL, 18.7 mmol). The reaction stirred under the ice bath for one hour. After which, 1-hexanol (5.04 mL, 42.4 mmol) was added in and the reaction was stirred from 0° C. to 20° C. for 16 hours. The reaction was diluted with 200 mL dichloromethane and washed by 100 mL of NaHCO₃ solution, water, brine, respectively. The organic was dried over Na₂SO₄, filtrated and purified by silica gel chromatography (0% ethyl acetate/hexane→20% ethyl acetate/hexane) to give title compound (Compound 43) (2.8 g). MS 562.7 (M+Na).

2-(hexyloxy)-2-[(9Z,12Z)-octadeca-9,12-dien-1-yloxy]ethanamine (Compound 44)

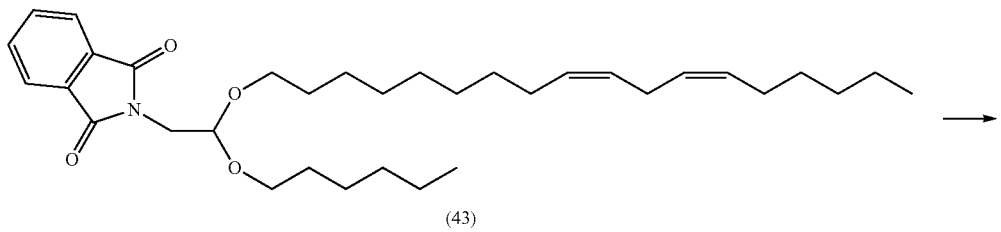

(43)

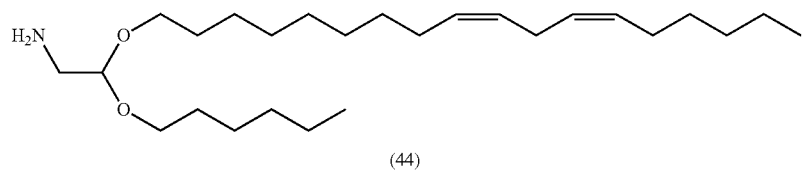

(44)

To 30 ml ethanol solution of 2-{2-(hexyloxy)-2-[(9Z,12Z)-octadeca-9,12-dien-1-yloxy]ethyl}-1H-isoindole-1,3(2H)-dione (compound 43) (2.75 g, 5.09 mmol was added 1.61 mL of methylhydrazine. The reaction was refluxed for 5 hours. The solvent was evaporated and the residue was retaken by 200 mL of hexane and filtrated. The solution was washed by 2×100 mL of NaHCO₃ solution, water and brine, respectively. The organic was dried over Na₂SO₄ and filtrated. Evaporation of solvent to dryness gave the title compound (2.01 g). MS 410.6 (M+1). HRMS 410.3980 (M+1). ¹H NMR δ (ppm) (CHCl₃-d): 5.41-5.30 (4 H, m), 4.39 (1 H, t, J=5.2 Hz), 3.65-3.60 (2 H, m), 3.48-3.43 (2 H, m), 2.78-2.76 (4 H, m), 2.07-2.00 (4 H, m), 1.61-1.55 (4 H, m), 1.35-1.29 (22 H, m), 0.90-0.87 (6 H, m).

2-[(9Z,12Z)-octadeca-9,12-dien-1-yloxy]-2-(octyloxy)ethanamine (Compound 45)

(45)

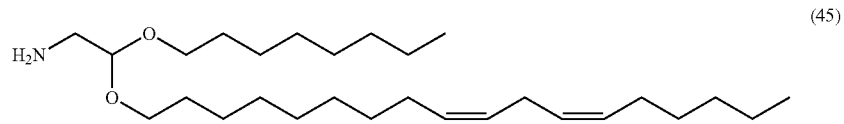 [SMILES: CCCCC/C=C\C/C=C\CCCCCCCCOC(CN)OCCCCCCCC]

Compound 45 was prepared according to General Scheme 10 as described for Compound 44. HRMS (M+1) calc'd: 438.4233; found: 438.4309.

2-(decyloxy)-2-[(9Z,12Z)-octadeca-9,12-dien-1-yloxy]ethanamine (Compound 46)

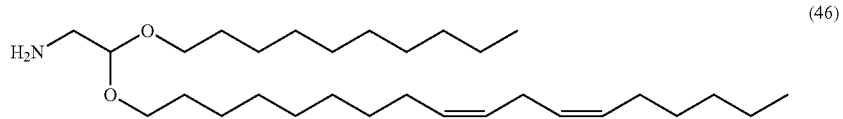 [SMILES: CCCCC/C=C\C/C=C\CCCCCCCCOC(CN)OCCCCCCCCCC]

Compound 46 was prepared according to General Scheme 10 as described for Compound 44. HRMS (M+1) calc'd: 466.4546; found: 466.4609.

2-(decyloxy)-2-[(9Z)-octadec-9-en-1-yloxy]ethanamine (Compound 47)

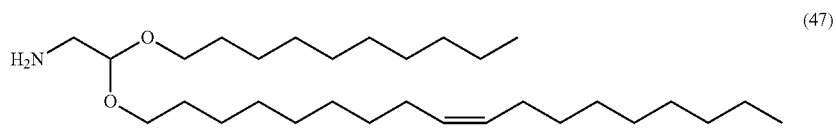 [SMILES: CCCCCCCC/C=C\CCCCCCCCOC(CN)OCCCCCCCCCC]

Compound 47 was prepared according to General Scheme 10 as described for Compound 44. HRMS (M+1) calc'd: 468.4702; found: 468.4763.

2-[(9Z,12Z)-octadeca-9,12-dien-1-yloxy]-2-(tetradecyloxy)ethanamine (Compound 48)

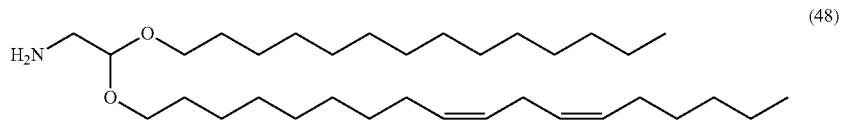 [SMILES: CCCCC/C=C\C/C=C\CCCCCCCCOC(CN)OCCCCCCCCCCCCCC]

Compound 48 was prepared according to General Scheme 10 as described for Compound 44. HRMS (M+1) calc'd: 522.5172; found: 522.5259.

[(2R)-1-{2,2-bis[(9Z,12Z)-octadeca-9,12-dien-1-yloxy]ethyl}pyrrolidin-2-yl]methanol (Compound 49)

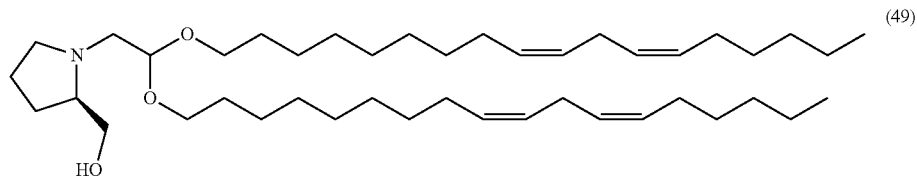 [SMILES: CCCCC/C=C\C/C=C\CCCCCCCCOC(CN1CCC[C@@H]1CO)OCCCCCCCC/C=C\C/C=C\CCCCC]

Compound 49 was prepared according to General Scheme 1 as described for Compound 2. HRMS (M+1) calc'd: 658.6060; found: 658.6128.
[(2S)-1-{2,2-bis[(9Z,12Z)-octadeca-9,12-dien-1-yloxy]ethyl}pyrrolidin-2-yl]methanol (Compound 50)
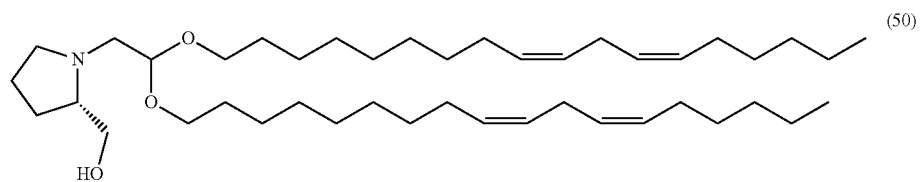 [SMILES: CCCCC/C=C\C/C=C\CCCCCCCCOC(CN1CCC[C@H]1CO)OCCCCCCCC/C=C\C/C=C\CCCCC]
Compound 50 was prepared according to General Scheme 1 as described for Compound 2. HRMS (M+1) calc'd: 658.6060; found: 658.6144.
tert-butyl (2S,4R)-2-{bis[(9Z,12Z)-octadeca-9,12-dien-1-yloxy]methyl}-4-hydroxypyrrolidine-1-carboxylate (Compound 52)
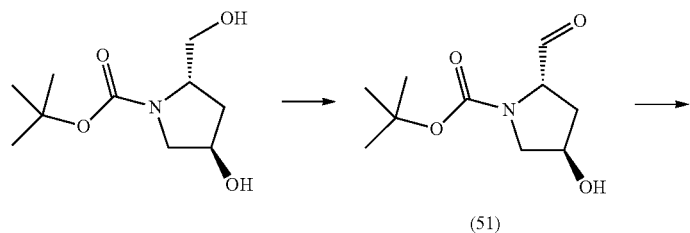
(51)
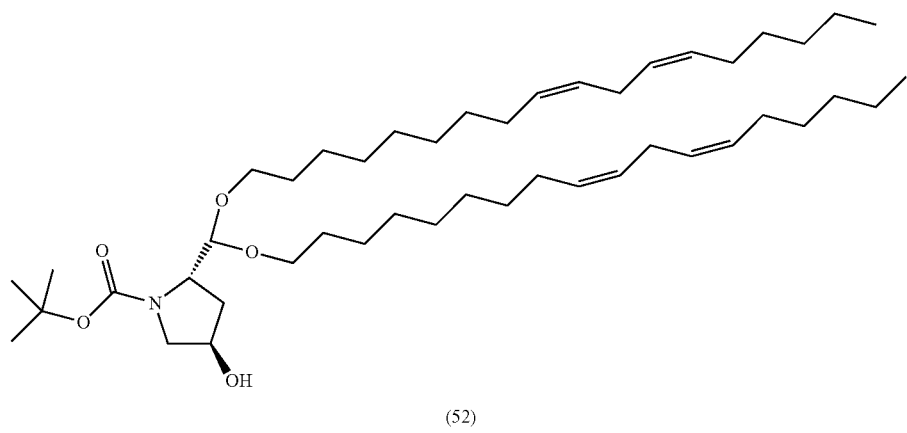
(52)

To 100 mL dichloromethane solution of tert-butyl (2S,4R)-4-hydroxy-2-(hydroxymethyl)pyrrolidine-1-carboxylate (5.86 g, 27 mmol) was added Dess-Martin periodinane (10.9 g, 25.6 mmol). After 5 h at ambient temperature, the reaction was diluted with another 200 mL dichloromethane. The dichloromethane solution was washed by 1×100 mL of 0.5 N $Na_2S_2O_3$ solution, saturated $NaHCO_3$ solution, water and brine. The organic was concentrated and the residue was purified by silica gel chromatography (0% EtOAC/hexane→70% EtOAc/hexane) to give tert-butyl (2S,4R)-2-formyl-4-hydroxypyrrolidine-1-carboxylate (3.5 g).

To tert-butyl (2S,4R)-2-formyl-4-hydroxypyrrolidine-1-carboxylate (3.4 g, 15.8 mmol) in (9Z,12Z)-octadeca-9,12-dien-1-ol (16.8 g, 63.2 mmol) was added pyridinium p-toluene-sulfonate (0.40 g, 1.58 mmol). After 16 h at 100° C., the reaction was purified directly by silica gel chromatography (0% EtOAC/hexane→35% EtOAc/hexane) to give title compound (1.9 g).). MS 752.8 (M+Na).

(3R,5S)-5-{bis[(9Z,12Z)-octadeca-9,12-dien-1-yloxy]methyl}pyrrolidin-3-ol (Compound 53)

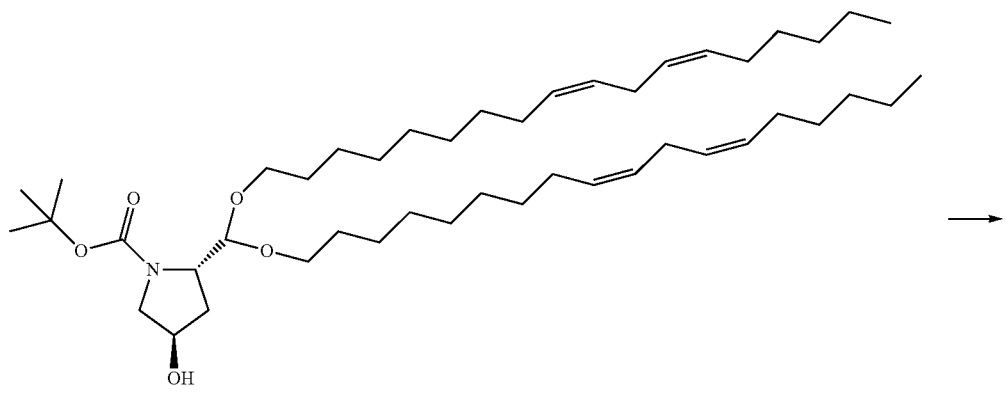

(52)

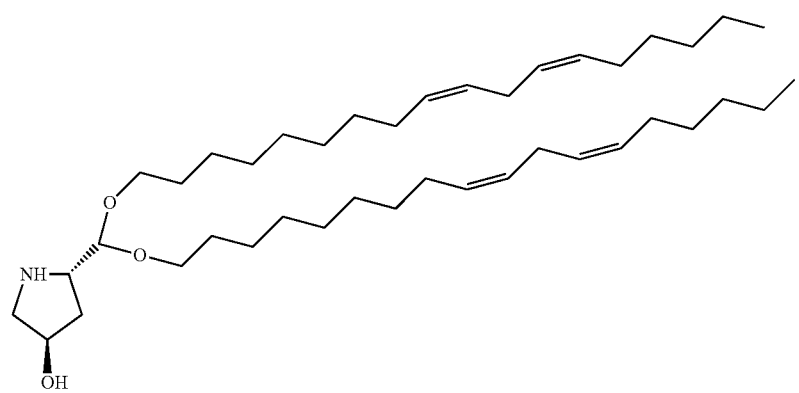

(53)

To 150 mL THF solution of tert-butyl (2S,4R)-2-{bis[(9Z, 12Z)-octadeca-9,12-dien-1-yloxy]methyl}-4-hydroxypyrrolidine-1-carboxylate (1.78 g, 2.44 mmol) was bubbled gas HCl for 3 minutes at 0° C. After that, the reaction was stirred from 0° C. to ambient temperature for 2 hours. The solvent was evaporated and the residue was retaken by 200 mL of dichloromethane and washed by 2×100 mL of NaHCO$_3$ solution, water and brine, respectively. The organic layer was concentrated and purified by reverse-phase HPLC (80%-100% CH$_3$CN/water) to give the title compound (0.32 g). MS 630.9 (M+1). HRMS 630.5817 (M+1). $^1$H NMR δ (ppm) (CHCl$_3$-d): 5.42-5.30 (8 H, m), 4.42-4.40 (1 H, m), 4.26-4.24 (1 H, m), 3.66-3.59 (2 H, m), 3.55-3.43 (3 H, m), 3.13-3.09 (1 H, m), 2.88-2.85 (1 H, m), 2.79-2.75 (4 H, m), 2.08-2.02 (8 H, m), 1.85-1.78 (4 H, m), 1.62-1.52 (4 H, m), 1.39-1.26 (32 H, m), 0.91-0.87 (6 H, m).

(2S)-2-amino-3,3-bis[(9Z,12Z)-octadeca-9,12-dien-1-yloxy]propan-1-ol (Compound 54)

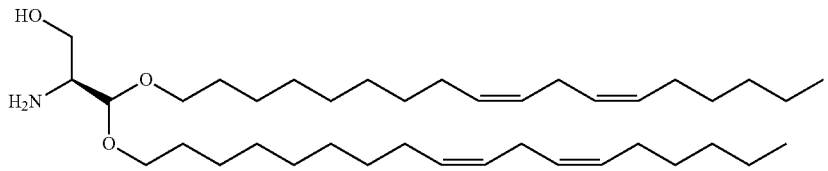

(54)

Compound 54 was prepared according to General Scheme 11 as described for Compound 53. HRMS (M+1) calc'd: 604.5590; found: 604.5675.

4-{bis[(9Z,12Z)-octadeca-9,12-dien-1-yloxy]methyl}piperidine (Compound 55)

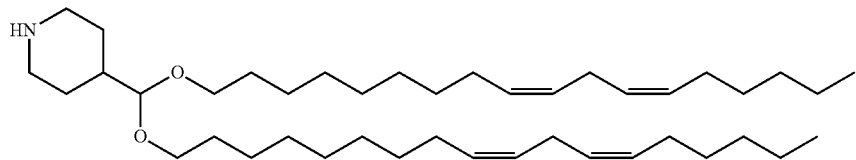

(55)

Compound 55 was prepared according to General Scheme 11 as described for Compound 53. HRMS (M+1) calc'd: 628.5954; found: 628.6042.

3-{bis[(9Z,12Z)-octadeca-9,12-dien-1-yloxy]methyl}piperidine (Compound 56)

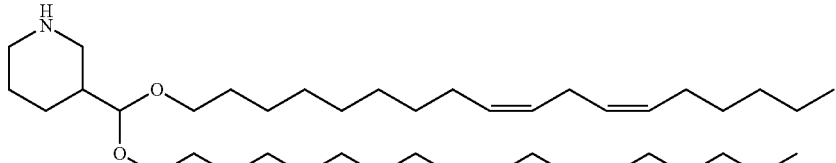

(56)

Compound 56 was prepared according to General Scheme 11 as described for Compound 53. HRMS (M+1) calc'd: 628.5954; found: 628.6017.

3-azido-1,1-bis[(9Z,12Z)-octadeca-9,12-dien-1-yloxy]propan-2-ol (Compound 60)

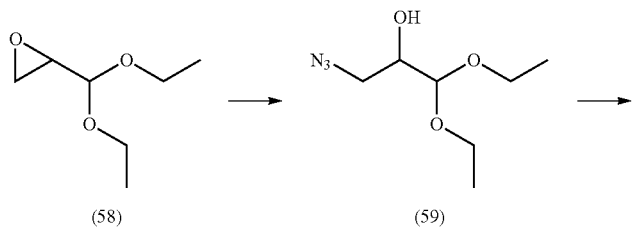

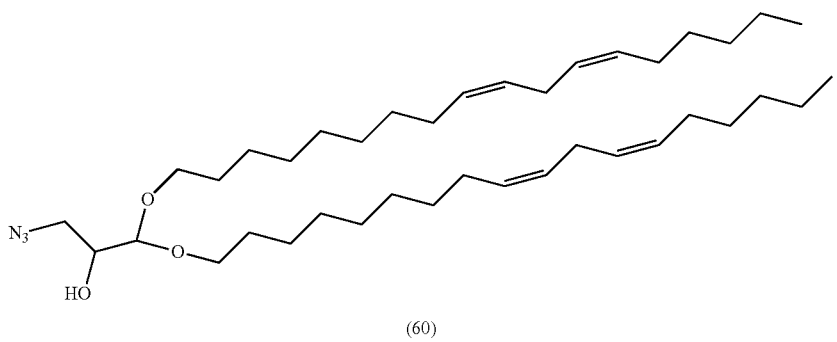

To the solution of 2-(diethoxymethyl)oxirane (4.79 mL, 30.8 mmol) in 80 mL of EtOH/pH 7.0 phosphate buffer 1:1 was added sodium azide (4.0 g, 61.6 mmol). The reaction was heated to 55° C. for 16 hours. The reaction was diluted with 300 mL of dichlormethane and washed by 2×100 mL of NaHCO$_3$ solution, water and brine, respectively. The organic was concentrated and purified by silica gel chromatography (0% MeOH/CH$_2$Cl$_2$→5% MeOH/CH$_2$Cl$_2$) to give 3-azido-1,1-diethoxypropan-2-ol (compound 59) (5.5 g).

To 3-azido-1,1-diethoxypropan-2-ol (compound 59) (2.80 g, 14.8 mmol) was added (9Z,12Z)-octadeca-9,12-dien-1-ol (15.1 mL, 48.8 mmol), followed by pPTS (0.37 g, 1.48 mmol). The reaction was heated to 80° C. for 16 hours. After which, the reaction was purified by reverse phase HPLC (70% 0.1% TFA-water/CH$_3$CN→100% CH$_3$CN) to give title compound (2.53 g). MS 652.8 (M+Na).

3-amino-1,1-bis[(9Z,12Z)-octadeca-9,12-dien-1-yloxy]propan-2-ol (Compound 61)

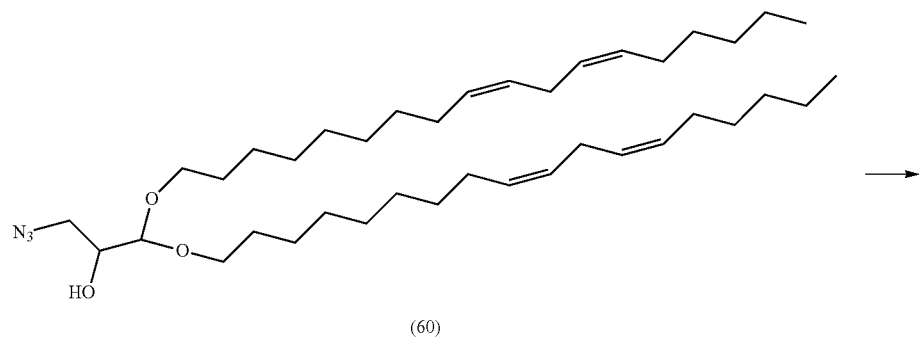

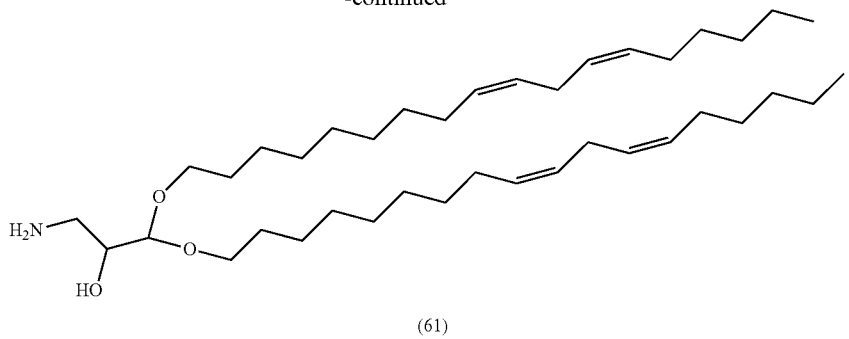

(61)

To 50 ml THF solution of 3-azido-1,1-bis[(9Z,12Z)-octadeca-9,12-dien-1-yloxy]propan-2-ol (compound 60) (2.56 g, 4.06 mmol) at 0° C. was added triphenylphosphine (3.52 g, 13.41 mmol). The reaction was stirred from 0° C. to 20° C. for 5 hours. After which, water (3 mL) was added into the reaction. The reaction was stirred at 55° C. for 16 h. The solvent was evaporated and the residue was retaken by 200 mL of hexane and filtrated. The hexane solution was washed by 2×100 mL of NaHCO₃ solution, water and brine, respectively. The organic was dried over Na₂SO₄ and filtrated. Evaporation of solvent to dryness gave the title compound (2.1 g). MS 604.8 (M+1). HRMS 604.5669 (M+1). ¹H NMR δ (ppm) (CHCl₃-d): 5.40-5.30 (8 H, m), 4.37 (1 H, d, J=5.9 Hz), 3.71-3.66 (2 H, m), 3.57-3.47 (3 H, m), 2.93-2.89 (1 H, m), 2.81-2.75 (4 H, m), 2.08-2.02 (8 H, m), 1.62-1.56 (4 H, m), 1.39-1.27 (34 H, m), 0.91-0.87 (6 H, m).

1-methyl-4,4-bis[(9Z,12Z)-octadeca-9,12-dien-1-yloxy]piperidine (Compound 62)

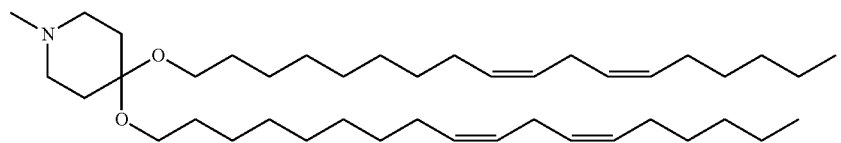

(62)

Combined ketone (1.0 g, 8.84 mmol), linoleyl alcohol (5.18 g, 19.44 mmol) and tosic acid (1.85 g, 9.72 mmol) and refluxed with a Dean-Stark trap for 3 hours. LCMS shows desired product but substantial unreacted alcohol. Approximately 500 mg of ketone added and additional ~500 mg of TsOH added and the reaction was refluxed for ~3 hours. Toluene removed in vacuo and loaded directly onto Torrent silica column. 100 DCM-->85 DCM/15 MeOH. Isolated fractions stripped down and then washed with aqueous NaOH and extracted into hexanes. Dried with Na2SO4 and solvent removed to afford light yellow oil. MS 628.8 (M+1). ¹H NMR δ (ppm) (CHCl₃-d): 5.37 (8H, m), 3.38 (4H, m), 2.78 (4H, m), 2.39 (4H, bs), 2.22 (3H, s), 2.02 (4H, m), 1.79 (4H, m), 1.53 (4H, m), 1.30 (36H, m), 0.86 (6H, m).

Compound 63 is DLinDMA as described in *J. Controlled Release*, 2005, 107, 276-287, US 2006/0083780 A1, and US 2006/0008910 A1.

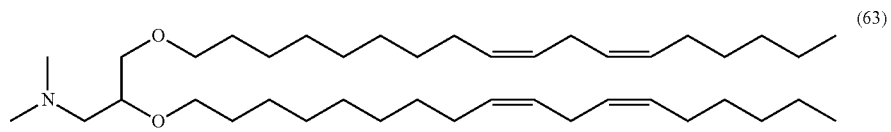 [SMILES: CCCCC/C=C\C/C=C\CCCCCCCCOCC(CN(C)C)OCCCCCCCC/C=C\C/C=C\CCCCC]

(63)

Compound 64 is DLinKC2DMA as described in *Nature Biotechnology*, 2010, 28, 172-176, WO 2010/042877 A1, WO 2010/048536 A2, WO 2010/088537 A2, and WO 2009/127060 A1.

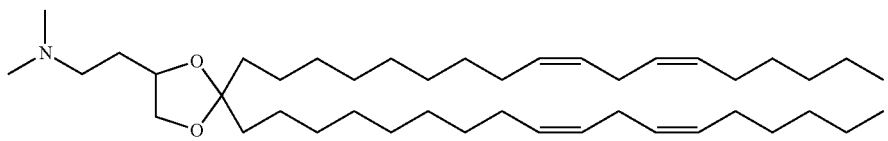

(64)

Utility

LNP Compositions

The following lipid nanoparticle compositions (LNPs) of the instant invention are useful for the delivery of oligonucleotides, specifically siRNA and miRNA:
Cationic Lipid/Cholesterol/PEG-DMG 56.6/38/5.4;
Cationic Lipid/Cholesterol/PEG-DMG 60/38/2;
Cationic Lipid/Cholesterol/PEG-DMG 67.3/29/3.7;
Cationic Lipid/Cholesterol/PEG-DMG 49.3/47/3.7;
Cationic Lipid/Cholesterol/PEG-DMG 50.3/44.3/5.4;
Cationic Lipid/Cholesterol/PEG-C-DMA/DSPC 40/48/2/10; and
Cationic Lipid/Cholesterol/PEG-DMG/DSPC 40/48/2/10.

LNP Process Description:

The Lipid Nano-Particles (LNP) are prepared by an impinging jet process. The particles are formed by mixing lipids dissolved in alcohol with siRNA dissolved in a citrate buffer. The mixing ratio of lipids to siRNA are targeted at 45-55% lipid and 65-45% siRNA. The lipid solution contains a novel cationic lipid of the instant invention, a helper lipid (cholesterol), PEG (e.g. PEG-C-DMA, PEG-DMG) lipid, and DSPC at a concentration of 5-15 mg/mL with a target of 9-12 mg/mL in an alcohol (for example ethanol). The ratio of the lipids has a mole percent range of 25-98 for the cationic lipid with a target of 35-65, the helper lipid has a mole percent range from 0-75 with a target of 30-50, the PEG lipid has a mole percent range from 1-15 with a target of 1-6, and the DSPC has a mole precept range of 0-15 with a target of 0-12. The siRNA solution contains one or more siRNA sequences at a concentration range from 0.3 to 1.0 mg/mL with a target of 0.3-0.9 mg/mL in a sodium citrate buffered salt solution with pH in the range of 3.5-5. The two liquids are heated to a temperature in the range of 15-40° C., targeting 30-40° C., and then mixed in an impinging jet mixer instantly forming the LNP. The teen) has a range from 0.25 to 1.0 mm and a total flow rate from 10-600 mL/min. The combination of flow rate and tubing ID has effect of controlling the particle size of the LNPs between 30 and 200 nm. The solution is then mixed with a buffered solution at a higher pH with a mixing ratio in the range of 1:1 to 1:3 vol:vol but targeting 1:2 vol:vol. This buffered solution is at a temperature in the range of 15-40° C., targeting 30-40° C. The mixed LNPs are held from 30 minutes to 2 hrs prior to an anion exchange filtration step. The temperature during incubating is in the range of 15-40° C., targeting 30-40° C. After incubating the solution is filtered through a 0.8 um filter containing an anion exchange separation step. This process uses tubing IDs ranging from 1 mm ID to 5 mm ID and a flow rate from 10 to 2000 mL/min. The LNPs are concentrated and diafiltered via an ultrafiltration process where the alcohol is removed and the citrate buffer is exchanged for the final buffer solution such as phosphate buffered saline. The ultrafiltration process uses a tangential flow filtration format (TFF). This process uses a membrane nominal molecular weight cutoff range from 30-500 KD. The membrane format can be hollow fiber or flat sheet cassette. The TFF processes with the proper molecular weight cutoff retains the LNP in the retentate and the filtrate or permeate contains the alcohol; citrate buffer; final buffer wastes. The TFF process is a multiple step process with an initial concentration to a siRNA concentration of 1-3 mg/mL. Following concentration, the LNPs solution is diafiltered against the final buffer for 10-20 volumes to remove the alcohol and perform buffer exchange. The material is then concentrated an additional 1-3 fold. The final steps of the LNP process are to sterile filter the concentrated LNP solution and vial the product.

Analytical Procedure:

1) siRNA Concentration

The siRNA duplex concentrations are determined by Strong Anion-Exchange High-Performance Liquid Chromatography (SAX-HPLC) using Waters 2695 Alliance system (Water Corporation, Milford Mass.) with a 2996 PDA detector. The LNPs, otherwise referred to as RNAi Delivery Vehicles (RDVs), are treated with 0.5% Triton X-100 to free total siRNA and analyzed by SAX separation using a Dionex BioLC DNAPac PA 200 (4×250 mm) column with UV detection at 254 nm. Mobile phase is composed of A: 25 mM $NaClO_4$, 10 mM Tris, 20% EtOH, pH 7.0 and B: 250 mM $NaClO_4$, 10 mM Tris, 20% EtOH, pH 7.0 with liner gradient from 0-15 min and flow rate of 1 ml/min. The siRNA amount is determined by comparing to the siRNA standard curve.

2) Encapsulation Rate

Fluorescence reagent SYBR Gold is employed for RNA quantitation to monitor the encapsulation rate of RDVs. RDVs with or without Triton X-100 are used to determine the free siRNA and total siRNA amount. The assay is performed using a SpectraMax M5e microplate spectrophotometer from Molecular Devices (Sunnyvale, Calif.). Samples are excited at 485 nm and fluorescence emission was measured at 530 nm. The siRNA amount is determined by comparing to the siRNA standard curve.

Encapsulation rate=(1−free siRNA/total siRNA)×100%

3) Particle Size and Polydispersity

RDVs containing 1 μg siRNA are diluted to a final volume of 3 ml with 1×PBS. The particle size and polydispersity of the samples is measured by a dynamic light scattering method using ZetaPALS instrument (Brookhaven Instruments Corporation, Holtsville, N.Y.). The scattered intensity is measured with He—Ne laser at 25° C. with a scattering angle of 90°.

4) Zeta Potential Analysis

RDVs containing 1 μg siRNA are diluted to a final volume of 2 ml with 1 mM Tris buffer (pH 7.4). Electrophoretic mobility of samples is determined using ZetaPALS instrument (Brookhaven Instruments Corporation, Holtsville, N.Y.) with electrode and He—Ne laser as a light source. The Smoluchowski limit is assumed in the calculation of zeta potentials.

5) Lipid Analysis

Individual lipid concentrations are determined by Reverse Phase High-Performance Liquid Chromatography (RP-HPLC) using Waters 2695 Alliance system (Water Corporation, Milford Mass.) with a Corona charged aerosol detector (CAD) (ESA Biosciences, Inc, Chelmsford, Mass.). Individual lipids in RDVs are analyzed using an Agilent Zorbax SB-C18 (50×4.6 mm, 1.8 μm particle size) column with CAD at 60° C. The mobile phase is composed of A: 0.1% TFA in H$_2$O and B: 0.1% TFA in IPA. The gradient changes from 60% mobile phase A and 40% mobile phase B from time 0 to 40% mobile phase A and 60% mobile phase B at 1.00 min; 40% mobile phase A and 60% mobile phase B from 1.00 to 5.00 min; 40% mobile phase A and 60% mobile phase B from 5.00 min to 25% mobile phase A and 75% mobile phase B at 10.00 min; 25% mobile phase A and 75% mobile phase B from 10.00 min to 5% mobile phase A and 95% mobile phase B at 15.00 min; and 5% mobile phase A and 95% mobile phase B from 15.00 to 60% mobile phase A and 40% mobile phase B at 20.00 min with flow rate of 1 ml/min. The individual lipid concentration is determined by comparing to the standard curve with all the lipid components in the RDVs with a quadratic curve fit. The molar percentage of each lipid is calculated based on its molecular weight.

Utilizing the above described LNP process, specific LNPs with the following ratios were identified:

Nominal Composition:
Cationic Lipid/Cholesterol/PEG-DMG 60/38/2
Cationic Lipid/Cholesterol/PEG-DMG 67.3/29/3.7.
Luc siRNA

```
                                              (SEQ.ID.NO.: 1)
5'-iB-AUAAGGCUAUGAAGAGAUATT-iB 3'

(SEQ.ID.NO.: 2)
3'-UUUAUUCCGAUACUUCUCUAU-5'
```

AUGC—Ribose
iB—Inverted deoxy abasic
  UC—2' Fluoro
  AGT—2' Deoxy
  AGU—2' OCH$_3$ Nominal Composition
Cationic Lipid/Cholesterol/PEG-DMG 60/38/2
Cationic Lipid/Cholesterol/PEG-DMG/DSPC 40/48/2/10
Cationic Lipid/Cholesterol/PEG-DMG/DSPC 58/30/2/10
ApoB siRNA

```
                                              (SEQ ID NO.: 3)
5'-iB-CUUUAACAAUUCCUGAAAUTsT-iB-3'

(SEQ ID NO.: 4)
3'-UsUGAAAUUGUUAAGGACUsUsUsA-5'
```

AUGC—Ribose
iB—Inverted deoxy abasic
  UC—2' Fluoro
  AGT—2' Deoxy
  AGU—2' OCH$_3$
UsA—phosphorothioate linkage Oligonucleotide synthesis is well known in the art. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). The Luc siRNA incorporated in the LNPs disclosed and utilized in the Examples were synthesized via standard solid phase procedures.

Example 1

In Vivo Evaluation of Efficacy and Toxicity

Figure 3:
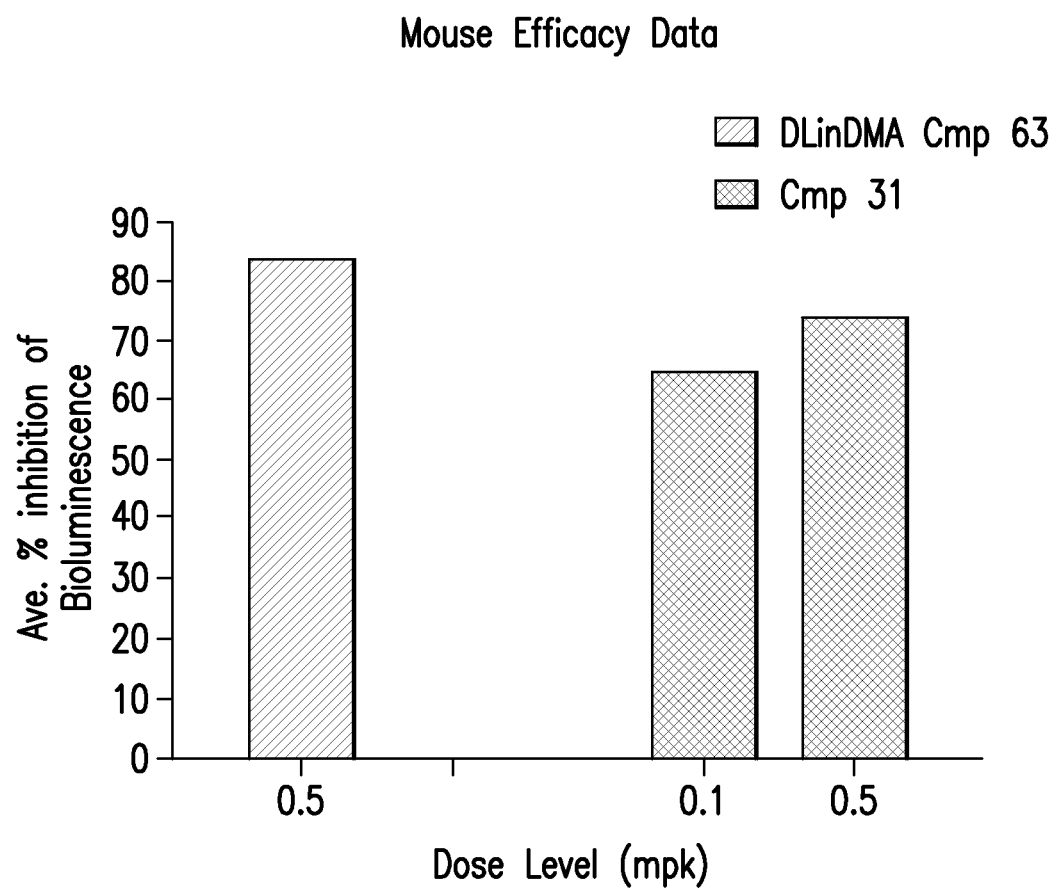
FIG. 3: Lipid (Compound 31) efficacy in mouse.

LNPs utilizing the compounds of the instant invention, in the nominal compositions described immediately above, were evaluated for in vivo efficacy and induction of inflammatory cytokines in a luciferase mouse model. The siRNA targets the mRNA transcript for the firefly (*Photinus pyralis*) luciferase gene (Accession # M15077). The primary sequence and chemical modification pattern of the luciferase siRNA is displayed above. The in vivo luciferase model employs a transgenic mouse in which the firefly luciferase coding sequence is present in all cells. ROSA26-LoxP-Stop-LoxP-Luc (LSL-Luc) transgenic mice licensed from the Dana Farber Cancer Institute are induced to express the Luciferase gene by first removing the LSL sequence with a recombinant Ad-Cre virus (Vector Biolabs). Due to the organo-tropic nature of the virus, expression is limited to the liver when delivered via tail vein injection. Luciferase expression levels in liver are quantitated by measuring light output, using an IVIS imager (Xenogen) following administration of the luciferin substrate (Caliper Life Sciences). Pre-dose luminescence levels are measured prior to administration of the RDVs. Luciferin in PBS (15 mg/mL) is intraperitoneally (IP) injected in a volume of 150 uL. After a four minute incubation period mice are anesthetized with isoflurane and placed in the IVIS imager. The RDVs (containing siRNA) in PBS vehicle were tail vein injected n a volume of 0.2 mL. Final dose levels ranged from 0.3 to 3 mg/kg siRNA. PBS vehicle alone was dosed as a control. Three hours post dose, mice were bled retro-orbitally to obtain plasma for cytokine analysis. Mice were imaged 48 hours post dose using the method described above. Changes in luciferin light output directly correlate with luciferase mRNA levels and represent an indirect measure of luciferase siRNA activity. In vivo efficacy results are expressed as % inhibition of luminescence relative to pre-dose luminescence levels. Plasma cytokine levels were determined using the SearchLight multiplexed cytokine chemiluminescent array (Pierce/Thermo). Systemic administration of the luciferase siRNA RDVs decreased luciferase expression in a dose dependant manner. Greater efficacy was observed in mice dosed with Compound 2 containing RDVs than with the RDV containing the octyl-CLinDMA cationic lipid, Compound 4, (Table 1). Similar efficacy was observed in mice dosed with Compound 31 containing RDVs than with RDV containing DLinDMA cationic lipid, Compound 63 (FIG. 3).

Table 1: Mouse In Vivo efficacy data. Average % Inhibition of Bioluminescence by LNPs prepared from Compound 2 compared against Compound 4 at 0.3 mg Kg$^{-1}$.

TABLE 1

| Compound 2 | Compound 4 |
|---|---|
| 64% | 55% |

Rat In Vivo Evaluation of Efficacy and Toxicity

Figure 4:
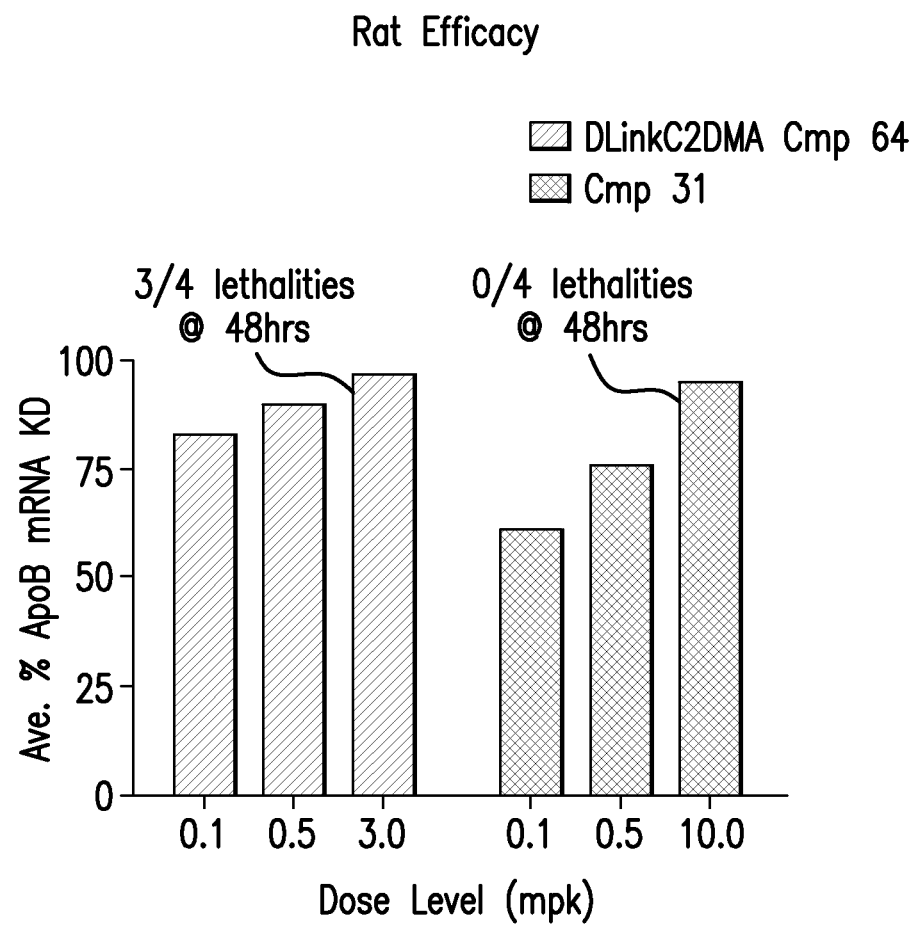
FIG. 4: Lipid (Compound 31) efficacy in rat.

LNPs utilizing compounds in the nominal compositions described above, were evaluated for in vivo efficacy and increases in alanine amino transferase and aspartate amino transferase in Sprague-Dawley (Crl:CD(SD) female rats (Charles River Labs). The siRNA targets the mRNA transcript for the ApoB gene (Accession # NM 019287). The primary sequence and chemical modification pattern of the ApoB siRNA is displayed above. The RDVs (containing siRNA) in PBS vehicle were tail vein injected in a volume of 1 to 1.5 mL. Infusion rate is approximately 3 ml/min. Five rats were used in each dosing group. After LNP administration, rats are placed in cages with normal diet and water present. Six hours post dose, food is removed from the cages. Animal necropsy is performed 24 hours after LNP dosing. Rats are anesthetized under isoflurane for 5 minutes, then maintained under anesthesia by placing them in nose cones continuing the delivery of isoflurane until ex-sanguination is completed. Blood is collected from the vena cava using a 23 gauge butterfly venipuncture set and aliquoted to serum separator vacutainers for serum chemistry analysis. Punches of the excised caudate liver lobe are taken and placed in RNALater (Ambion) for mRNA analysis. Preserved liver tissue was homogenized and total RNA isolated using a Qiagen bead mill and the Qiagen miRNA-Easy RNA isolation kit following the manufacturer's instructions. Liver ApoB mRNA levels were determined by quantitative RT-PCR. Message was amplified from purified RNA utilizing a rat ApoB commercial probe set (Applied Biosystems Cat # RN01499054_ml). The PCR reaction was performed on an ABI 7500 instrument with a 96-well Fast Block. The ApoB mRNA level is normalized to the housekeeping PPIB (NM 011149) mRNA. PPIB mRNA levels were determined by RT-PCR using a commercial probe set (Applied Biosystems Cat. No. Mm00478295_ml). Results are expressed as a ratio of ApoB mRNA/PPIB mRNA. All mRNA data is expressed relative to the PBS control dose. Serum ALT and AST analysis were performed on the Siemens Advia 1800 Clinical Chemistry Analyzer utilizing the Siemens alanine aminotransferase (Cat#03039631) and aspartate aminotransferase (Cat#03039631) reagents. Similar efficacy and better tolerability was observed in rats dosed with Compound 31 containing RDV than with the RDV containing the DLinKC2DMA cationic lipid 64 (FIG. 4).

Determination of Cationic Lipid Levels in Rat Liver

Liver tissue was weighed into 20-ml vials and homogenized in 9 v/w of water using a GenoGrinder 2000 (OPS Diagnostics, 1600 strokes/min, 5 min). A 50 µL aliquot of each tissue homogenate was mixed with 300 µL of extraction/protein precipitating solvent (50/50 acetonitrile/methanol containing 500 nM internal standard) and the plate was centrifuged to sediment precipitated protein. A volume of 200 µL of each supernatant was then transferred to separate wells of a 96-well plate and 10 µl samples were directly analyzed by LC/MS-MS.

Standards were prepared by spiking known amounts of a methanol stock solution of Compound 1 or OCD into untreated rat liver homogenate (9 vol water/weight liver). Aliquots (50 µL) each standard/liver homogenate was mixed with 300 µL of extraction/protein precipitating solvent (50/50 acetonitrile/methanol containing 500 nM internal standard) and the plate was centrifuged to sediment precipitated protein. A volume of 200 µL of each supernatant was transferred to separate wells of a 96-well plate and 10 µl of each standard was directly analyzed by LC/MS-MS.

Figure 5:
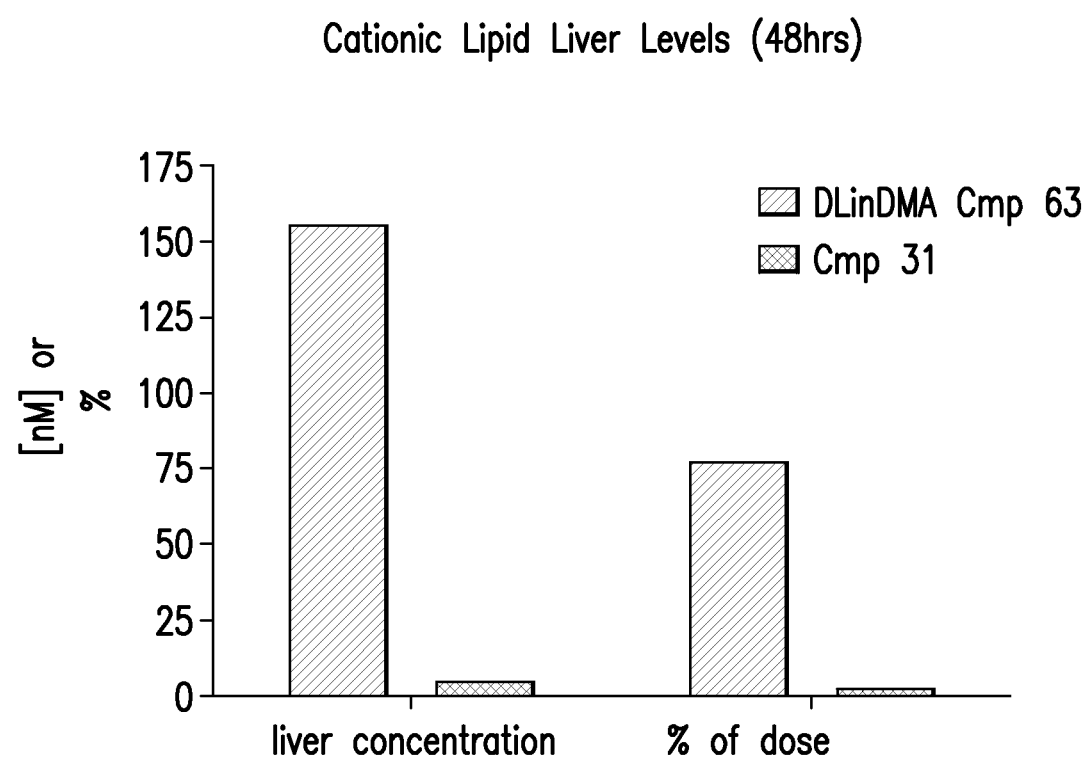
FIG. 5. Absolute liver levels of cationic lipid (Compound 31) in rat at 48 hours.

Absolute quantification versus standards prepared and extracted from rat liver homogenate was performed using an Aria LX-2 HPLC system (Thermo Scientific) coupled to an API 4000 triple quadrupole mass spectrometer (Applied Biosystems). For each run, a total of 10 µL sample was injected onto a BDS Hypersil C8 HPLC column (Thermo, 50×2 mm, 3 µm) at ambient temperature (FIG. 5).

Mobile Phase A: 95% H2O/5% methanol/10 mM ammonium formate/0.1% formic acid Mobile Phase B: 40% methanol/60% n-propanol/10 mM ammonium formate/0.1% formic acid The flow rate was 0.5 mL/min and gradient elution profile was as follows: hold at 80% A for 0.25 min, linear ramp to 100% B over 1.6 min, hold at 100% B for 2.5 min, then return and hold at 80% A for 1.75 min. Total run time was 5.8 min. API 4000 source parameters were CAD: 4, CUR: 15, GS1: 65, GS2: 35, IS: 4000, TEM: 550, CXP: 15, DP: 60, EP: 10.

Rhesus Monkey In Vivo Evaluation of Efficacy

Figure 6:
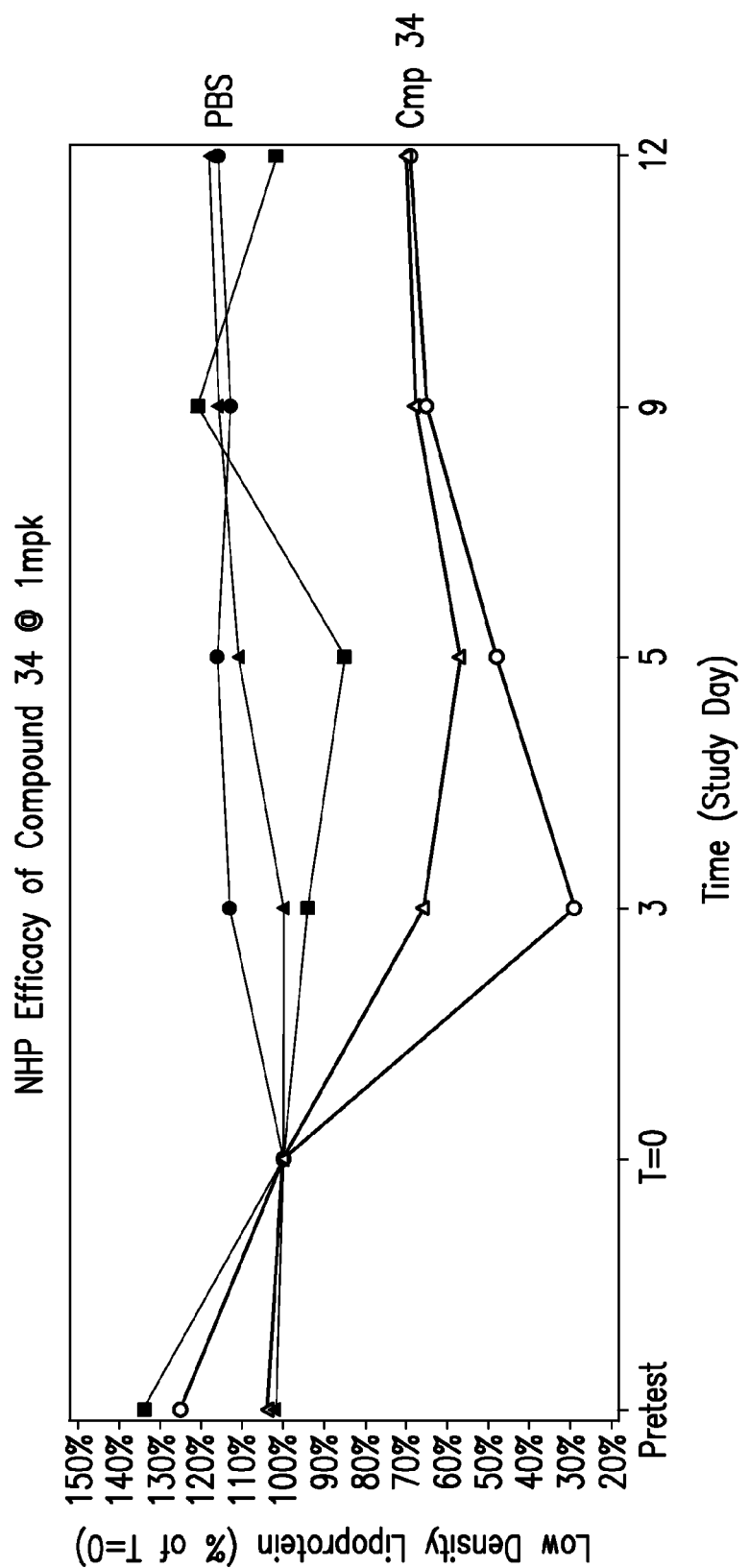
FIG. 6: Lipid (Compound 34) efficacy in NHP.

LNPs utilizing compound 34 in the nominal compositions described above, were evaluated for in vivo efficacy in male or female *Macaca mulatta* (rhesus) monkeys. The siRNA targets the mRNA transcript for the ApoB gene (Accession # XM 001097404). The primary sequence and chemical modification pattern of the ApoB siRNA is displayed above. The RDVs (containing siRNA) in PBS vehicle were administered by intravenous injection in the saphenous vein at an injection rate of 20 mL/minute to a dose level of 1 mg/kilogram siRNA. The injection volumes were from 1.9 to 2.1 mL/kilogram and monkeys ranged in weight from 2.5 to 4.5 kilograms. The RDV or PBS control were administered to three monkeys. At multiple days post dose, 1 mL blood samples were drawn from the femoral artery for serum chemistry analysis. Monkeys were fasted overnight prior to blood draws. As a measure of efficacy, LDL-C was monitored as a downstream surrogate marker of ApoB mRNA reduction. At 2-12 days post systemic administration of RDVs containing compound 34, serum levels of LDL-C were reduced to less than 30% of pre-dose levels (FIG. 6).

In Vitro Evaluation of Hydrolytic Stability

Stability of acetal/ketal di-linoleyl cationic lipids were evaluated under three pH conditions (5.0, 6.0, and 7.5).

A: Incubation Procedures:

Incubation mixtures (600 µL total volume) containing 10 µM test compound, 50% (v/v) methanol, 50% (v/v) various pH buffers (pH 5.0, 20 mM sodium acetate buffer; pH 6.0: 20 mM sodium acetate buffer; and pH 7.5: 20 mM sodium hydrogen phosphate buffer). The reaction mixture was incubated at 37° C. with gentle shaking. A 50 µL aliquot was removed at time: 0, 30 min, 1 hr, 4 hr and 24 hr, and transferred to a collection tube containing 200 µL reaction stopping buffer (95% H$_2$O/5% methanol/10 mM ammonium formate/0.1% formic acid with 500 nM internal standard). After a brief vortex and a 10 min centrifugation at 1000 g at 4'C., 100 µL of the supernatants were transferred to a 96-well plate, followed a 10 fold dilution with reaction stopping buffer. 10 µL samples were directly injected and analyzed by LC/MS-MS.

B. LC-MS/MS Analysis:

Absolute quantification was performed using a Perkin Elmer HPLC system coupled to an API 4000 triple quadrupole mass spectrometer (Applied Biosystems). For each run, a total of 10 μL of sample was injected onto a Phenomenex Luna C18(2) HPLC column (5 μm, 50×2 mm) with the temperature set to 50° C. (column heater, Restek, Model PTC050). A dual eluent system was used: 95% $H_2O$/5% methanol/10 mM ammonium formate/0.1% formic acid (A) and 40% methanol/60% n-propanol/10 mM ammonium formate/0.1% formic acid (B). The flow rate was 0.4 mL/min and the gradient was as follows: hold at 100% A for 1 min, ramp to 0% A at 2.5 min, hold at 0% A for 2 min, then hold at 100% A for 1.5 min. Total run time was 7.0 min.

The API 4000 instrument source parameters were CAD: 4, CUR: 15, GS1: 65, GS2: 35, IS: 4000, TEM: 600, DP: 80, CE: 29, CXP: 10, EP: 10, and the ion-transition condition was 602.7/336.3.

What is claimed is:

1. A cationic lipid of Formula A:

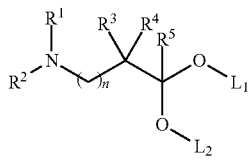

wherein:
n is 0, 1 or 2;
$R^1$ and $R^2$ are independently selected from H and ($C_1$-$C_4$)alkyl, wherein said alkyl is optionally substituted with one or more substituents selected from R', or $R^1$ and $R^2$ can be taken together with the nitrogen to which they are attached to faun a monocyclic heterocycle which is optionally substituted with one or more substituents selected from R';
$R^3$ is selected from H and ($C_1$-$C_4$)alkyl, wherein said alkyl is optionally substituted with one or more substituents selected from R', or $R^3$ can be taken together with $R^1$ to form a monocyclic heterocycle which is optionally substituted with one or more substituents selected from R', or $R^3$ can be taken together with $R^4$ to form cyclopropyl or cyclobutyl;
$R^4$ is selected from H and ($C_1$-$C_4$)alkyl, said alkyl is optionally substituted with one or more substituents selected from R';
$R^5$ is selected from H and ($C_1$-$C_4$)alkyl, or $R^5$ can be taken together with $R^1$ to form a monocyclic heterocycle which is optionally substituted with one or more substituents selected from R';
R' is independently selected from halogen, R'' and OR'';
R'' is selected from H and ($C_1$-$C_4$)alkyl, wherein said alkyl is optionally substituted with one or more substituents selected from halogen and OH;
$L_1$ is a $C_6$-$C_{18}$ alkyl or a $C_6$-$C_{18}$ alkenyl; and
$L_2$ is a $C_4$-$C_{22}$ alkenyl;
or any pharmaceutically acceptable salt or stereoisomer thereof.

2. The cationic lipid of claim 1, wherein $L_2$ is $C_{18}$ alkenyl.

3. The cationic lipid of claim 2, wherein $L_2$ is

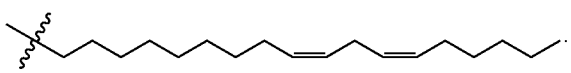

4. A cationic lipid of Formula A according to claim 1, wherein:
$L_1$ and $L_2$ are

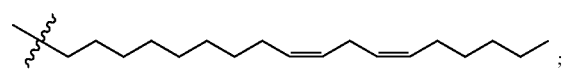 [SMILES: *CCCCCCCC/C=C\C/C=C\CCCCC]

and
all other variables are as defined in claim 1;
or any pharmaceutically acceptable salt or stereoisomer thereof.

5. A cationic lipid according to claim 1 which is selected from:
N,N-dimethyl-2,2-bis[(9Z,12Z)-octadeca-9,12-dien-1-yloxy]ethanamine;
N,N-dimethyl-2,2-bis[(9Z,12Z)-octadeca-9,12-dien-1-yloxy]propan-1-amine;
2,2-bis[(9Z,12Z)-octadeca-9,12-dien-1-yloxy]ethanamine;
(2R)-2-{bis[(9Z,12Z)-octadeca-9,12-dien-1-yloxy]methyl}pyrrolidine;
(2R)-2-{bis[(9Z,12Z)-octadeca-9,12-dien-1-yloxy]methyl}-1-methylpyrrolidine;
2-[(2R)-2-{bis[(9Z,12Z)-octadeca-9,12-dien-1-yloxy]methyl}pyrrolidin-1-yl]ethanol;
(2S)-1,1-bis[(9Z,12Z)-octadeca-9,12-dien-1-yloxy]propan-2-amine;
2-methyl-1,1-bis[(9Z,12Z)-octadeca-9,12-dien-1-yloxy]propan-2-amine;
4,4-bis[(9Z,12Z)-octadeca-9,12-dien-1-yloxy]piperidine; and
3,3-bis[(9Z,12Z)-octadeca-9,12-dien-1-yloxy]pyrrolidine;
N,N-dimethyl-3,3-bis[(9Z,12Z)-octadeca-9,12-dien-1-yloxy]propan-1-amine;
1-{3,3-bis[(9Z,12Z)-octadeca-9,12-dien-1-yloxy]propyl}pyrrolidine;
3,3-bis[(9Z,12Z)-octadeca-9,12-dien-1-yloxy]propan-1-amine;
N,N-dimethyl-2,2-bis[(9Z)-octadec-9-en-1-yloxy]ethanamine;
1-{bis[(9Z,12Z)-octadeca-9,12-dien-1-yloxy]methyl}cyclopropanamine;
N,N-dimethyl-2-[(9Z,12Z)-octadeca-9,12-dien-1-yloxy]-2-(octyloxy)ethanamine;
2-(decyloxy)-N,N-dimethyl-2-[(9Z,12Z)-octadeca-9,12-dien-1-yloxy]ethanamine;
2-[(8Z)-dodec-8-en-1-yloxy]-N,N-dimethyl-2-[(9Z,12Z)-octadeca-9,12-dien-1-yloxy]ethanamine;
1-{2-[(8Z)-dodec-8-en-1-yloxy]-2-[(9Z,12Z)-octadeca-9,12-dien-1-yloxy]ethyl}pyrrolidine;
1-{2-[(9Z,12Z)-octadeca-9,12-dien-1-yloxy]-2-(octyloxy)ethyl}pyrrolidine;
[(2S)-1-{2-(decyloxy)-2-[(9Z,12Z)-octadeca-9,12-dien-1-yloxy]ethyl}pyrrolidin-2-yl]methanol;
1-{2-(decyloxy)-2-[(9Z,12Z)-octadeca-9,12-dien-1-yloxy]ethyl}piperidin-4-ol;
N,N-dimethyl-3-[(9Z,12Z)-octadeca-9,12-dien-1-yloxy]-3-(octyloxy)propan-1-amine;
2-(heptyloxy)-N,N-dimethyl-2-[(9Z,12Z)-octadeca-9,12-dien-1-yloxy]ethanamine;
N,N-dimethyl-2-(nonyloxy)-2-[(9Z,12Z)-octadeca-9,12-dien-1-yloxy]ethanamine;
1-{3-[(9Z,12Z)-octadeca-9,12-dien-1-yloxy]-3-(octyloxy)propyl}pyrrolidine;
2-(hexyloxy)-2-[(9Z,12Z)-octadeca-9,12-dien-1-yloxy]ethanamine;
2-[(9Z,12Z)-octadeca-9,12-dien-1-yloxy]-2-(octyloxy)ethanamine;
2-(decyloxy)-2-[(9Z,12Z)-octadeca-9,12-dien-1-yloxy]ethanamine;
2-(decyloxy)-2-[(9Z)-octadec-9-en-1-yloxy]ethanamine;
2-[(9Z,12Z)-octadeca-9,12-dien-1-yloxy]-2-(tetradecyloxy)ethanamine;
[(2R)-1-{2,2-bis[(9Z,12Z)-octadeca-9,12-dien-1-yloxy]ethyl}pyrrolidin-2-yl]methanol;
[(2S)-1-{2,2-bis[(9Z,12Z)-octadeca-9,12-dien-1-yloxy]ethyl}pyrrolidin-2-yl]methanol;

(3R,5S)-5-{bis[(9Z,12Z)-octadeca-9,12-dien-1-yloxy]methyl}pyrrolidin-3-ol;

(2S)-2-amino-3,3-bis[(9Z,12Z)-octadeca-9,12-dien-1-yloxy]propan-1-ol;

4-{bis[(9Z,12Z)-octadeca-9,12-dien-1-yloxy]methyl}piperidine;

3-{bis[(9Z,12Z)-octadeca-9,12-dien-1-yloxy]methyl}piperidine;

3-amino-1,1-bis[(9Z,12Z)-octadeca-9,12-dien-1-yloxy]propan-2-ol; and 1-methyl-4,4-bis[(9Z,12Z)-octadeca-9,12-dien-1-yloxy]piperidine or any pharmaceutically acceptable salt or stereoisomer thereof.

6. A lipid nanoparticle comprising a cationic lipid according to claim 1.

7. The lipid nanoparticle according to claim 6 further comprises an siRNA or miRNA.

\* \* \* \* \*